United States Patent
Li et al.

(10) Patent No.: US 12,211,589 B2
(45) Date of Patent: Jan. 28, 2025

(54) METHOD FOR IDENTIFYING BASE IN NUCLEIC ACID AND SYSTEM

(71) Applicant: GeneMind Biosciences Company Limited, Shenzen (CN)

(72) Inventors: Linsen Li, Shenzen (CN); Huan Jin, Shenzen (CN); Zefei Jiang, Shenzen (CN); Lei Sun, Shenzen (CN)

(73) Assignee: GeneMind Biosciences Company Limited, Shenzen (CN)

( * ) Notice: Subject to any disclaimer, the term of this patent is extended or adjusted under 35 U.S.C. 154(b) by 396 days.

(21) Appl. No.: 17/787,824

(22) PCT Filed: Sep. 10, 2020

(86) PCT No.: PCT/CN2020/114355
§ 371 (c)(1),
(2) Date: Jun. 21, 2022

(87) PCT Pub. No.: WO2021/120715
PCT Pub. Date: Jun. 24, 2021

(65) Prior Publication Data
US 2023/0027811 A1    Jan. 26, 2023

(30) Foreign Application Priority Data

Dec. 21, 2019 (CN) .......................... 201911331502.1

(51) Int. Cl.
*G16B 30/10* (2019.01)
*G06T 7/33* (2017.01)
*G06T 7/73* (2017.01)

(52) U.S. Cl.
CPC .............. *G16B 30/10* (2019.02); *G06T 7/337* (2017.01); *G06T 7/74* (2017.01); *G06T 2207/20021* (2013.01); *G06T 2207/20221* (2013.01)

(58) Field of Classification Search
CPC ........ G16B 30/10; G16B 40/10; G16B 30/00; G06T 7/337; G06T 7/74; G06T 2207/20021; G06T 2207/20221
(Continued)

(56) References Cited

U.S. PATENT DOCUMENTS 5,674,743 A * 10/1997 Ulmer ............... B01L 3/502776
                                                   436/172
2006/0073501 A1* 4/2006 Van Den Boom ... C12Q 1/6869
                                                   435/6.12
(Continued)

FOREIGN PATENT DOCUMENTS

| CN | 107918931 A | 4/2018 |
| CN | 108192953 A | 6/2018 |
| CN | 209759461 U | 12/2019 |

OTHER PUBLICATIONS

Born et al., "Principles of Optics: Electromagnetic Theory of Propagation, Interference and Diffraction of Light," *Cambridge University Press* 7:334, 1999.
(Continued)

*Primary Examiner* — Negussie Worku
(74) *Attorney, Agent, or Firm* — Seed Intellectual Property Law Group LLP

(57) ABSTRACT

A method for identifying a base in nucleic acid, a computer-readable storage medium, a computer program product, and a system. The method for identifying a base in nucleic acid comprises: mapping a coordinate of each bright spot in a bright spot set corresponding to a template onto an image to be inspected, and determining the position of a corresponding coordinate on said image (S11); determining the intensity of a signal at the position of the corresponding coordinate on said image, the intensity being a corrected intensity (S21); and comparing the intensity of the signal at the position of the corresponding coordinate on said image with
(Continued)

the size of a first preset value, and determining a base type corresponding to the position on the basis of the comparison result, so as to achieve base calling (S31). The method may quickly and accurately identify a base, and achieve the determination of an order of nucleotides/bases of at least part of a sequence of a template.

20 Claims, 15 Drawing Sheets

(58) Field of Classification Search
USPC .......................................................... 382/129
See application file for complete search history.

(56) References Cited

U.S. PATENT DOCUMENTS

| 2012/0020537 | A1  | 1/2012 | Garcia et al. | |
|---|---|---|---|---|
| 2014/0055135 | A1* | 2/2014 | Nielsen ................. | G01R 33/58 |
| | | | | 324/309 |
| 2015/0004610 | A1* | 1/2015 | Cantor ................. | C12Q 1/6818 |
| | | | | 435/6.11 |
| 2015/0243028 | A1* | 8/2015 | Garcia ................. | G06T 7/0012 |
| | | | | 382/129 |
| 2020/0074630 | A1* | 3/2020 | Garcia .................... | G06T 7/248 |
| 2020/0129005 | A1* | 4/2020 | Zanchetta ............. | A47J 36/321 |
| 2021/0055365 | A1* | 2/2021 | Hoshiyama ...... | G01R 33/56572 |
| 2022/0051407 | A1* | 2/2022 | Garcia ................. | G06T 7/0014 |

OTHER PUBLICATIONS

Ewing et al., "Base-Calling of Automated Sequencer Traces Using Phred. I. Accuracy Assessment," *Genome Res.* 3:175-185, 1998.
Chinese Office Action, dated Sep. 2, 2022, for Chinese Patent Application No. 201911331502.1. (9 pages).
Translation of International Search Report of International Application PCT/CN2020/114355, mailed on Nov. 27, 2020. (2 pages).

* cited by examiner

|   | 1 | 2 | 3 |   |
|---|---|---|---|---|
| 7 |   |   |   | 4 |
| 8 |   | midS |   | 5 |
| 9 |   |   |   | 6 |
|   | 10 | 11 | 12 |   |

*FIG. 3*

|   | (x-1, y+2) | (x, y+2) | (x+1, +2) |   |
|---|---|---|---|---|
| (x-2, y+1) |   |   |   | (x+2, y+1) |
| (x-2, y) |   | (x, y) |   | (x+2, y) |
| (x-2, y-1) |   |   |   | (x+2, y-1) |
|   | (x-1, y-2) | (x, y-2) | (x+1, y-2) |   |

METHOD FOR IDENTIFYING BASE IN NUCLEIC ACID AND SYSTEM

CROSS REFERENCE TO RELATED APPLICATIONS

The present application claims priority and benefit to Chinese Patent Application No. CN 201911331502.1 filed with China National Intellectual Property Administration on Dec. 21, 2019, which is incorporated herein by reference in its entirety.

TECHNICAL FIELD

The present application relates to the field of data processing, and in particular to a method for calling bases in a nucleic acid, a computer readable storage medium, a computer program product and a system.

BACKGROUND

In the related art, the sequencing generally refers to determining the primary structure or sequence of biopolymers, including nucleic acids (such as DNA and RNA), and includes the process of determining the order of the nucleotides or bases (adenine A, guanine G, thymine T or uracil U, and cytosine C) of a given nucleic acid fragment. Such methods typically involve calling the bases at one or more positions in a nucleic acid (i.e., basecalling) to determine the sequence of the nucleic acid.

The change in signal and/or signal intensity corresponding to the incorporation of a nucleotide or base to a specific position of a target nucleic acid molecule (template) may be indicative of the base type at that position on the nucleic acid molecule. For example, different bases may be called by fluorescent molecules differently labeled. The incorporating of a nucleotide or base to a specific position of a target nucleic acid molecule, also referred to as the incorporation of a nucleotide or base into a target nucleic acid molecule or the base extension, can be achieved, for example, by polymerization, ligation, hybridization, and the like.

In particular, for platforms that use an optical imaging system to acquire images of signals of base extension multiple times and perform nucleic acid sequencing based on processing the images, accurate basecalling based on image processing is often difficult due to the effect of optical effects, spatial effects, and/or chemical reactions (such as chromatic aberration, crosstalk, and/or phasing) on image acquisition, localization, and/or signal intensity.

Therefore, how to process information including correlating images acquired at different time points to effectively and accurately determine the type and order of at least part of the nucleotides or bases of a template nucleic acid is a problem desired to be solved or improved.

SUMMARY

Embodiments of the present application are intended to at least solve, to some extent, one of the technical problems existing in the prior art or at least provide a useful means. To this end, embodiments of the present application provide a method for calling one or more bases in a nucleic acid, a computer-readable storage medium, a computer program product and a system.

In one embodiment of the present application, provided is a method for calling one or more bases in a nucleic acid by detecting an image obtained from sequencing, which comprises: aligning coordinates of each spot in a spot set corresponding to a template to an image to be detected to determine a position of corresponding coordinates in the image to be detected; determining intensity of a signal of the position of the corresponding coordinates on the image to be detected, the intensity being corrected intensity; and comparing the intensity of the signal of the position of the corresponding coordinates on the image to be detected with a first preset value, and determining a base type corresponding to the position based on a comparison result to realize the basecalling.

The spot set corresponding to the template is constructed based on a set of images, and each image in the set of images comprises a plurality of spots; the set of images and the image to be detected are all from sequencing and correspond to a same field of view, the set of images are from at least one cycle of sequencing, and at least a part of the signals are shown as at least a part of the spots on the set of images.

Other embodiments of the present application relate to a computer-readable medium, a computer product, a computer program product and a system related to the method in the above embodiment.

For example, in one embodiment of the present application, provided is a computer-readable storage medium configured for storing a program executed by a computer, and executing the program comprises implementing the method for calling one or more bases in a nucleic acid according to any of the aforementioned embodiments.

In one embodiment of the present application, provided is a computer product comprising the computer-readable storage medium according to any of the aforementioned embodiments.

In one embodiment of the present application, provided is a system, which comprises the computer product according to any of the aforementioned embodiments and one or more processors configured for executing a program stored in the computer-readable storage medium. Executing the program comprises implementing the method for basecalling according to any of the aforementioned embodiments.

In one embodiment of the present application, provided is a computer program product comprising an instruction for calling one or more bases in a nucleic acid, and the instruction causes a computer to execute the method for basecalling according to any of the aforementioned embodiments when the program is executed by the computer.

In one embodiment of the present application, provided is a system configured for performing the method for calling bases in a nucleic acid according to any of the aforementioned embodiments.

In one embodiment of the present application, provided is a system, which comprises a plurality of modules configured for performing the steps of the method for calling bases in a nucleic acid according to any of the aforementioned embodiments.

The type and format of the image to be detected, i.e., the original input data, are not particularly limited in the method, product and/or system for calling bases in a nucleic acid according to any of the above embodiments of the present application, and the image to be detected may be from any platform for sequencing nucleic acids based on optical imaging detection, including but not limited to the second and third generation sequencing platforms, such as one or more series of sequencing platforms from such institutions as BGI (including CG (Complete Genomics)), Illumina, PacBio (Pacific Biosciences), ThermoFisher (including Life technologies), Roche and Helicos.

The method, product and/or system of any of the embodiments of the present application allows for rapid and accurate basecalling and enables the determination of the order of nucleotides or bases of at least a part of the sequence of the template.

The additional aspects and advantages of the embodiments of the present application will be partially set forth in the following description, and will partially become apparent from the following description or be appreciated by practice of the embodiments of the present application.

BRIEF DESCRIPTION OF THE DRAWINGS

The aforementioned and/or additional aspects and advantages of embodiments of the present application will become apparent and easily understood from the description of the embodiments in reference to the following drawings, among which:

FIG. 3 shows a schematic 5×5 matrix according to an embodiment of the present application;

FIG. 4 shows a schematic 5×5 convolution kernel according to an embodiment of the present application;

FIG. 8 shows a schematic diagram illustrating at least a part of offsets of combinations of two corresponding blocks after dividing two images into 100×100 blocks according to an embodiment of the present application;

DETAILED DESCRIPTION

Figure 1:
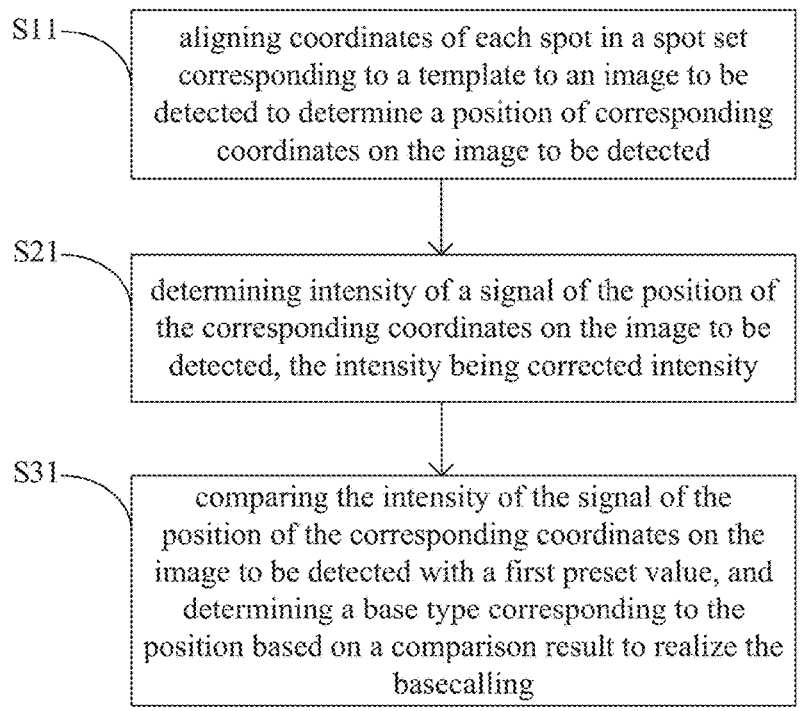
FIG. 1 shows a schematic flowchart of a method for calling one or more bases in a nucleic acid according to an embodiment of the present application.

The embodiments of the present application are described in detail below, and the examples of the embodiments are shown in the accompanying drawings, throughout which identical or similar reference numerals represent identical or similar elements or elements having identical or similar functions. The embodiments described below by reference to the accompanying drawings are exemplary and are merely intended to explain the present application rather than be construed as limiting the present application.

In the embodiments of the present application, it should be understood that the terms "first" and "second" are used for description purpose only rather than being construed as indicating or implying relative importance or implicitly indicating the number of indicated technical features; the features defined with "first" and "second" may explicitly or implicitly include one or more of the features. Unless otherwise specified, "a group" or "a plurality of" means two or more.

It should be noted that unless otherwise specified, "connect" and "interconnect" should be comprehended in their broad sense. For example, "connect" may be "fixedly connect", "detachably connect" or "integrally connect"; "mechanically connect", "electrically connect" or "communicate with each other"; or "directly interconnect", "indirectly interconnect through an intermediate", "the communication between the interiors of two elements" or "the interaction between two elements". For those of ordinary skill in the art, the specific meanings of the aforementioned terms in corresponding examples can be understood according to specific conditions.

The present application may repeat reference numbers and/or reference letters in different examples. Such repetition is intended for simplicity and clarity rather than for indicating the relationship between various embodiments and/or settings discussed.

In embodiments of the present application, the "sequencing", "nucleic acid sequencing" and "gene sequencing" are used interchangeably and refer to nucleic acid sequence determination, including sequencing by synthesis (SBS) and/or sequencing by ligation (SBL), including DNA sequencing and/or RNA sequencing, including long fragment sequencing and/or short fragment sequencing (the long fragment and short fragment are defined relatively; for example, nucleic acid molecules longer than 1 Kb, 2 Kb, 5 Kb or 10 Kb may be referred to as long fragments, and nucleic acid molecules shorter than 1 Kb or 800 bp may be referred to as short fragments), and including paired-end sequencing, single-read sequencing, mate-pair sequencing, and/or the like (the paired-end sequencing or mate-pair sequencing may refer to the reading of any two segments or portions of the same nucleic acid molecule that are not completely overlapping); the sequencing involves the process of introducing or incorporating one or more nucleotides (including nucleotide analogues) to the template and acquiring the corresponding signals.

Sequencing generally involves multiple cycles of sequencing to determine the order of multiple nucleotides or bases on the template; "one cycle of sequencing", also referred to as "sequencing cycle", may be defined as completion of the base extensions of the four types of nucleotides or bases once, and in other words, as the determination of the base type at any given position on the template. For sequencing platforms that realize sequencing based on polymerization or ligation reactions, one cycle of sequencing comprises incorporation of four types of nucleotides (including nucleotide analogues) to the template once and the acquisition of corresponding signals; for platforms that realize sequencing based on polymerization reaction, a reaction system comprises reaction substrate nucleotides, polymerase and a template, a sequence fragment (a sequencing primer) is bound to the template, and on the basis of a base pairing principle and a polymerization reaction principle, the added reaction substrate nucleotide is polymerized to the sequencing primer under the catalysis of the polymerase to realize the incorporation of the nucleotide to a specific position of the template. Generally, one cycle of sequencing may comprise one or more base extensions (repeats). For example, four types of nucleotides are sequentially added to the reaction system to each perform base extension and corresponding acquisition of reaction signals, and one cycle of sequencing comprises four base extensions; for another example, four types of nucleotides are added into the reaction system in any combinations (such as in pairs or in one-three combinations), the two combinations each perform base extension and corresponding acquisition of reaction signals, and one cycle of sequencing comprises two base extensions; for yet another example, four types of nucleotides are added simultaneously to the reaction system for base extension and reaction signal acquisition, and one cycle of sequencing comprises one base extension.

The "spot" on an image, also referred to as "peak", "bright dot" or "light dot", refers to a position on an image where the signal is relatively strong, e.g., where the signal is stronger than the surrounding signals, appearing as a relatively bright speckle or dot on the image. A spot or its location occupies one or more pixels. The signal of spot or position may come from the target molecule or from non-target substance. Detection of "spots" includes detection of the optical signal from a target molecule, such as an extended base or base cluster.

The "chromatic aberration" (CA) refers to the optical phenomenon that a lens cannot optically focus various wavelengths of chromatic light onto the same point (position) (Max Born; Emil Wolf Principles of Optics: Electromagnetic Theory of Propagation, Interference and Diffraction of Light (7th Edition). Cambridge University Press. Oct. 13, 1999: 334. ISBN 0521642221.); in imaging, chromatic aberration occurs when each color on the spectrum fails to focus on the same position along the optical axis. For a sequencing platform that involves imaging the same object (e.g., one or more nucleic acid molecules) with multiple wavelengths of chromatic light, at least, chromatic aberration causes the object to have different positions or coordinates in multiple images of the object acquired at different wavelengths, or the object does not actually move, but it appears to move in multiple images at different wavelengths due to chromatic aberration.

The "crosstalk", also referred to as "laser-crosstalk" or "spectra-crosstalk", refers to the phenomenon that the signal corresponding to one base diffuses into the signal of another base; for sequencing platforms that use fluorescent molecules labeled differently to identify different bases, it may be detected that the signal of one fluorescent molecule diffuses into another fluorescent channel in one cycle of sequencing if the emission spectra of two or more selected fluorescent molecules overlap.

The "phasing", "phase imbalance", "dephasing" or "phase diversity" refers to the phenomenon of asynchrony of reactions between nucleic acid molecules in a group, such as a cluster of nucleic acid molecules, in a chemical reaction, including phasing or sequence lag and phasing or sequence lead, and it is, in a sequencing platform that uses fluorescence molecules labeled differently to identify different bases, shown as the phenomenon that the signal of the fluorescent molecule corresponding to the base at a specific position is not zero in more than one cycle of sequencing. In general, sequencing is performed using nucleotides that are labeled with fluorescent molecules and have a blocking group. The blocking group on a nucleotide may prevent other nucleotides from incorporating to the next position on the template, and is, for example, an azido group attached to the 3' position of the nucleotide's glycosyl, and either dropping of the blocking group or failing to remove the blocking group prior to the next base extension will result in phasing.

In embodiments of the present application, the image is from a platform that performs nucleic acid sequencing based on an optical imaging detection flowcell, and the platform includes, but is not limited to, one or more series of sequencing platforms from such companies or institutions as BGI/CG (Complete Genomics), Illumina/Solexa, ThermoFisher/Life Technologies/ABI SOLiD, and Roche 454.

In some platforms, multiple sequence fragments (probes or sequencing primers) are immobilized on a solid phase support such as a flowcell, and a template (target nucleic acid molecule) is connected to the flowcell by binding to the probes (e.g., by hybridization). Optionally, amplification of the template is performed on the flowcell, followed by loading of the flowcell bearing the template into a sequencing apparatus that comprises an imaging system and a fluid path system. Solutions containing polymerase and nucleotide, respectively, are introduced to the flowcell by controlling the fluid path system, and a controlled polymerase chain reaction is performed under suitable conditions; for example, the nucleotide contained in a nucleotide solution introduced includes a modified nucleotide with a blocking group and a fluorescent molecule, and based on the complementary base pairing rule, it binds to a specific position of a certain template under the catalysis of polymerase, and the blocking group thereon is capable of preventing other nucleotides (including modified nucleotides) from incorporating to the next position of the template; further, the fluorescent molecules are excited by using an imaging system to enable the fluorescent molecules to emit fluorescent signals, and the fluorescent signals are acquired, for example, photographing a reaction area on the flowcell, to obtain images; finally, by controlling the fluid path system, a cleavage reagent is introduced to remove the blocking group and the fluorescent molecule of the modified nucleotide bound to the template; at this point, one base extension is completed, and the solutions containing the polymerase and the nucleotide, respectively, are introduced again to the flowcell, and the base reaction described above is repeated. Based on the photographed images and the time sequence of the photographing operations and/or the type of base added, the type of nucleotide or base bound to a specific position of the template each time is determined, i.e., the nucleotides or bases at these specific positions of the template are determined.

Given that the efficiency of the reaction in each step of a biochemical reaction is less than one hundred percent, for example, even if the modified nucleotides not bound to the template are removed before signal acquisition, e.g., by washing the reaction areas on the flowcell with a buffer that does not affect base extension, it can be understood that, the positions on the acquired image that appear as spots, in addition to possibly being corresponding to the modified nucleotides bound to the template, may also correspond to modified nucleotides or fluorescent molecules that are not bound to the template but have not been removed, and may also correspond to signals emitted by non-target substances in the detection area on the flowcell.

In one embodiment of the present application, the image is from a second generation sequencing platform, such as the Illumina HiSeq/MiSeq series and the BGI MGISeq series, the input raw data are the position, intensity and other related parameters of the acquired signals, including information about the pixels of the image, and the detection of the "spots" on the image includes the detection of optical signals corresponding to the cluster of nucleic acid molecules.

Referring to FIG. 1, provided is, according to an embodiment of the present application, a method for calling one or more bases in a nucleic acid by detecting an image obtained from sequencing, which comprises: S11, aligning coordinates of each spot in a spot set corresponding to a template to an image to be detected to determine a position of corresponding coordinates on the image to be detected; S21, determining intensity of a signal of the position of the corresponding coordinates on the image to be detected, the intensity being corrected intensity; and S31, comparing the intensity of the signal of the position of the corresponding coordinates on the image to be detected with a first preset value, and determining a base type corresponding to the position based on a comparison result to realize the basecalling.

The spot set corresponding to the template is constructed based on a set of images, and each image in the set of images comprises a plurality of spots; the set of images and the image to be detected are all from sequencing and correspond to a same field of view (FOV), the set of images are from at least one cycle of sequencing, and at least a part of the signals are shown as at least a part of the spots on the set of images.

The method can rapidly and accurately call the bases, and further rapidly and accurately determine the order of nucleotides or bases of at least a part of the sequence of the template.

Specifically, in S11, the spot set corresponding to the template includes a plurality of spots corresponding to the template, including intensity and coordinate information of each spot.

The coordinate aligning is to establish a mapping relationship between an original image, such as a spot set corresponding to a template, and a target image, such as an image to be detected, and the mapping relationship includes the determination of the coordinate position of any spot of the original image on the target image after alignment.

The method for determining the coordinates and the method for implementing the coordinate aligning are not limited in this embodiment. Coordinate aligning can be implemented, for example, by a remap function in Opencv. For determining the coordinates of the spots, generally, a spot on the image occupies one or more pixels, and the coordinates of a certain pixel may be used as the coordinates of the spot, or the sub-pixel center coordinates of the spot may be determined as the coordinates of the spot by using, for example, a quadratic function interpolation method.

Specifically, in some embodiments, the input image to be detected may be a 16-bit tiff image of 512×512 or 2048× 2048, and a tiff image may be a grayscale image. For a grayscale image, the pixel value refers to the grayscale value. The input image may also be a color image, and each pixel of the color image has three pixel values. The color image may be converted into a grayscale image for subsequent processing and detection, so as to reduce the calculation and complexity in image processing. A non-grayscale image may be converted into a grayscale image with methods including but not limited to floating point algorithm, integer method, shift method, mean value method, etc.

The spot set corresponding to the template may be constructed during the implementation of basecalling or may be constructed and stored in advance. Herein, a set of images acquired from at least one cycle of sequencing are used to pre-construct a spot set corresponding to the template, which is stored for later use.

In some examples, the four types of nucleotides carry different labels that are excited to emit signals with different colors when sequencing is performed, and the different signals correspond to different types of nucleotides or bases. The spot set corresponding to the template includes four spot sets corresponding to four types of nucleotides, respectively.

In one example, construction of a spot set corresponding to the template using a set of images from one cycle of sequencing comprises: sequentially or simultaneously adding four types of nucleotides into a reaction system for one cycle of sequencing to obtain a set of images, where the set of images comprise a first image, a second image, a third image and a fourth image, the first image, the second image, the third image and the fourth image are respectively acquired from signals by the four types of nucleotides during reaction, and the reaction system comprises a template and polymerase; performing spot detection for the first image, the second image, the third image and the fourth image separately to determine the spots of the images, including coordinates of the spots; aligning the set of images such that the spots of the set of images are in a same coordinate system; merging the spots on the aligned set of images to obtain a primary spot set; and establishing spot sets corresponding to the four types of nucleotides, respectively, based on the primary spot set, namely establishing templates of the four types of nucleotides or bases.

When constructing the spot set corresponding to the template, the order for performing spot detection on the set of images and aligning the set of images is not limited. The alignment of the set of images may be performed with or without the spots on the set of images. For example, marks can be made at specific positions of the detection area, and the set of images can be aligned according to the information of the marks of each image.

The one cycle of sequencing may comprise four base extensions; for example, four types of nucleotides are sequentially added into the reaction system to independently perform the base extension, including the acquisition of corresponding reaction signals. It may also comprise two base extensions; for example, four types of nucleotides are combined in pairs, and the nucleotides in each combination are added into the reaction system simultaneously to perform the base extension. It may also comprise only one base extension; for example, four types of nucleotides are added simultaneously to perform the base extension in the reaction system.

In one example, the four types of nucleotides are added simultaneously into the reaction system, and corresponding reaction signals are acquired by an imaging system to obtain the set of images and/or the image to be detected. The imaging system comprises a first laser, a second laser, a first camera, and a second camera.

Further, the template is DNA, and the four types of nucleotides carry a first label, a second label, a third label and a fourth label, respectively, for example, four fluorescent molecules with different emission spectra or incompletely overlapped emission spectra; in one cycle of sequencing: the first laser is used for exciting nucleotides, two of the four nucleotides emit a first signal and a second signal, respectively, and the first camera and the second camera synchronously operate and acquire the first signal and the second signal, respectively, to obtain the first image and the second image; and, the second laser is used for exciting nucleotides, the other two nucleotides of the four nucleotides emit a third signal and a fourth signal, respectively, and the first camera and the second camera synchronously operate and acquire the third signal and the fourth signal, respectively, to obtain the third image and the fourth image. The first laser and the second laser may be from two laser devices capable of emitting different wavelengths, or may be from one laser device capable of emitting multiple wavelengths.

Figure 2:
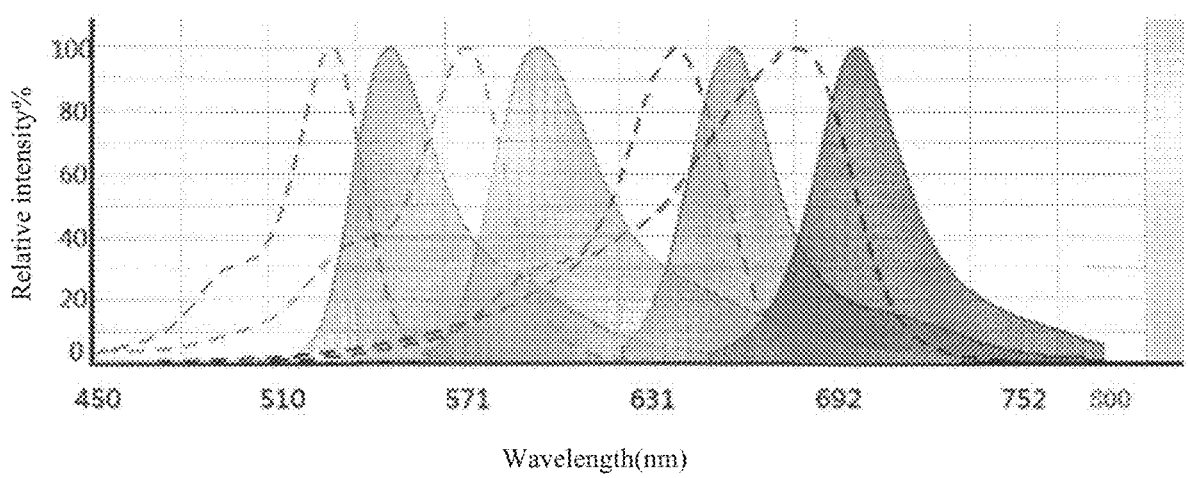
FIG. 2 shows spectral curves of four fluorescent dyes according to an embodiment of the present application.

Specifically, for example, four deoxyribonucleotides dATP (sometimes abbreviated as A), dTTP (sometimes abbreviated as T), dGTP (sometimes abbreviated as G) and dCTP (sometimes abbreviated as C) carry four fluorescent dyes of ATTO-532, ROX, CY5 and IF700, respectively. Spectral curves of the four fluorescent dyes are shown in FIG. 2. Dashed curves from left to right are absorption spectra of ATTO-532, ROX, CY5 and IF700, respectively, the peak wavelengths of which being 531 nm, 577 nm, 651 nm and 692 nm, respectively, and solid curves from left to right are radiation spectraor emission spectra of ATTO-532, ROX, CY5 and IF700, respectively, the peak wavelengths of which being 551 nm, 602 nm, 670 nm and 712 nm, respectively. When the light path structure of the imaging system is designed, the excitation efficiency of dyes is considered. Lasers with at least two wavelengths are adopted to excite the four dyes in pairs in a time-sharing manner, and two cameras are used for acquiring fluorescent signals in a time-sharing manner via a dichroic mirror beam splitter and a double-band-pass filter; in other words, the first laser and the second laser can work asynchronously, and the first camera and the second camera can work synchronously, so that the excitation of the four dyes and the acquisition of corresponding signals can be realized efficiently.

The identification and detection of spots on the image is to detect signals from the target molecules. The method for detecting the spots is not limited in this embodiment of the present application, and the detection can be performed, for example, by referring to the method disclosed in CN107918931A.

In some embodiments, detecting the spots comprises detecting each image in the set of images using a $k1 \times k2$ matrix, which comprises: determining that a matrix with a relation midS between central intensity and edge intensity meeting a first preset condition corresponds to a spot; the central intensity reflects intensity of a central area of the matrix, the edge intensity reflects intensity of an edge area of the matrix, the central area and the edge area form the $k1 \times k2$ matrix, $k1$ and $k2$ are both natural numbers greater than 1, and the $k1 \times k2$ matrix comprises $k1 \times k2$ pixels.

The values of $k1$ and $k2$ are related to the density and distribution of the template molecules on the solid substrate and the imaging resolution, and it is generally desired that the size of the $k1 \times k2$ matrix should be not smaller than the size of a target spot, which corresponds to a target signal or a target molecule or molecule cluster; preferably, it is also generally desired that the size of the $k1 \times k2$ matrix should be smaller than the size of two independent spots on the image.

In the $k1 \times k2$ matrix, $k1$ and $k2$ may or may not be equal. Generally, the value ranges of $k1$ and $k2$ are both greater than 1 and less than 10.

In one example, related parameters of an imaging system includes: a 60×magnification for an objective lens, a size of 6.5 μm for an electronic sensor, the smallest identifiable size (resolution) of 0.1 μm for a microscopic image acquired by the electronic sensor, a 16-bit grayscale or color image of 512×512, 1024×1024 or 2048×2048 for an output or input image, a target spot being corresponding to a single molecule (usually less than 10 nm, including one or a few molecules or nucleic acid fragments, generally less than 10 molecules, e.g., 1, 2, 3, 4 or 5 molecules), and a target spot occupying about 3×3 pixels on the image.

In another example, related parameters of an imaging system includes: a 20×magnification for an objective lens, a resolution of 0.3 μm for a microscopic image acquired by the electronic sensor, a grayscale or color image of 512×512, 1024×1024, 2048×2048 or 2560×2048 for an output or input image, a spot being corresponding to a molecule cluster, and a spot occupying about 5×5 pixels on the image.

$k1$ and $k2$ may be odd numbers or even numbers, and in some embodiments, $k1$ and $k2$ are both odd numbers. In this way, the setting of the central area and the edge area of the matrix and the subsequent calculation are facilitated.

In one example, $k1=k2=3$.

The central area and the edge area are relatively defined. For example, an area of a certain size centered on a central pixel or central sub-pixel of the matrix may be the central area, while the other area constitutes the edge area of the matrix.

The intensity or signal intensity, including the central intensity and the edge intensity herein, is generally related to the values of the pixel when described in an image. For example, it is the pixel value of one or more pixels, the average or median of multiple pixel values, the sum of multiple pixel values, or in a positive correlation with the pixel value.

In some examples, the first preset condition is that midS≥S1, midS=midInt−sumInts(1: n)/n. midInt represents the central intensity, sumInts(1: n)/n represents the edge intensity, sumInts(1: n) represents the sum of pixel values of the $1^{st}$ to $N^{th}$ pixels of the edge area, n is a natural number not less than 4, and S1 is any value of [2, 4]. The first preset condition is obtained by the inventor through training with a large amount of image data, and it is suitable for spot detection of images with different signal intensities, spot densities and distributions from various sequencing platforms.

Specifically, k1 and k2 are both odd numbers greater than 3, and the central area is a 3×3 area centered on a central pixel of the matrix. In one example, referring to FIG. 3, k1=k2=5. FIG. 3 illustrates a 5×5 matrix. The central area is a 3×3 area centered on a pixel marked with midS in the figure, a pixel value of any pixel in the central area is the intensity of the central area (central intensity) (for example, a pixel value of the pixel marked with midS in the figure is the central intensity), n is 12 (shown as the pixels marked with 1 to 12 in the figure), and S1 is 2. In this way, the spots corresponding to the target molecules can be quickly and effectively detected, which is favorable for constructing a spot set corresponding to the template and for subsequent accurate basecalling.

In other embodiments, the spot detection comprises: convolving each image of the set of images to obtain convolved images; searching for all pixels containing peak values in a k3×k4 area in the convolved images, k3 and k4 being both natural numbers greater than 1, and the k3×k4 area containing k3×k4 pixels of the convolved images; and determining that a k5×k6 area meeting a second preset condition and centering on a peak pixel corresponds to a spot, the second preset condition being that a pixel value of the peak pixel of the k5×k6 area is not less than S2, k5 and k6 being both natural numbers greater than 1, and S2 being capable of being determined based on pixels of the convolved image.

The convolution kernel, also called convolution mask, filter, filter mask or scanning window, is used to convolve the images, and the method for performing convolution is not limited in this embodiment; for example, the convolution is performed using correlation function in Matlab after the convolution kernel is set. When an image is convolved, the calculation process typically comprises the steps of optionally turning a convolution mask over, sliding the convolution mask on the original image, multiplying the elements at corresponding positions, and adding them together to obtain the final result. For example, generally filtering may be implemented using a Gaussian template.

In some examples, the target molecule is a nucleic acid molecule cluster, e.g., a nucleic acid molecule cluster formed by amplification (such as strand displacement amplification or bridge amplification) of a nucleic acid molecule, the resolution of the imaging system for image acquisition is about 0.3 μm, and it is set that k3=k4=k5=k6=5; further, after studying the laws of the shape and/or intensity variations of a large number of such target molecules on images, the inventors set a 5×5 convolution kernel to perform the convolution, and the 5×5 convolution kernel is shown in FIG. 4. Each mark on the convolution kernel shown in FIG. 4 represents the coordinates or positions of the pixel where the mark is located with respect to the central pixel, and the horizontal direction is expressed as x, the vertical direction is expressed as y, and the unit is pixel. Performing the convolution operation on the image using such a 5×5 convolution kernel includes performing reassignment for each pixel in the image using the convolution kernel. In this way, the difference between the central pixels and the edge pixels (e.g., the outermost peripheral pixels) of the 5×5 area in the image can be enhanced. Specifically, in one example, based on a large number of training data, the inventors set the intensity value or pixel value of the position or pixel without the coordinate mark on the convolution kernel shown in FIGS. 4 to 0, and after performing the convolution operation set forth below through the convolution kernel, for example, the intensity value or pixel value Ints(x,y) of a pixel with coordinates (x, y) in the image becomes newInts (x,y): newInts (x,y)=(12×Ints(x,y)−Edge8Ints(x,y,2))×200/ (Ints(x,y)+Edge8Ints(x,y,2)). Int(x,y) represents the pixel value or intensity value of the pixel or position with coordinates (x, y) before convolution; to facilitate fast operation, the range of newInts(x,y) can be further set to [0, 255], and newInts (x,y) is assigned to be 0 in the case of being less than 0, and it is assigned to be 255 in the case of being greater than 255;

Edge8Ints(x,y,2) represents the sum of pixel values or intensity values of 12 pixels not less than 2 pixels away from the central coordinates (x,y) in 8 directions (8 adjacent areas) of the central coordinates (x,y), and in this example, the 12 pixels not less than 2 pixels away from the central coordinates (x,y) are shown as the pixels with coordinate marks in FIG. 4, and Edge8Ints(x, y,2) can be represented as Edge8Ints(x,y,2)=(Ints(x−2, y−1)+Ints(x−2, y)+Ints(x−2, y+1)+Ints(x+2, y−1)+Ints(x+2, y)+Ints(x+2, y+1)+Ints(x−1, y−2)+Ints(x,y−2)+Ints(x+1, y−2)+Ints(x−1, y+2)+Ints(x,y+2)+Ints(x+1, y+2)), and Ints(x−2, y−1), Ints(x−2, y), Ints(x−2, y+1), Ints(x+2, y−1), Ints(x+2, y), Ints(x+2, y+1), Ints(x−1, y−2), Ints(x,y−2), Ints(x+1, y−2), Ints(x−1, y+2), Ints(x, y+2) and Ints(x+1, y+2) represent intensity values or pixel values of the positions or pixels with coordinates (x−2, y−1), (x−2, y), (x−2, y+1), (x+2, y−1), (x+2, y), (x+2, y+1), (x−1, y−2), (x,y−2), (x+1, y−2), (x−1, y+2), (x,y+2) and (x+1, y+2) before convolution, respectively.

Before performing the convolution, optionally, Gaussian filtering of the image is performed; and the convolution operation is performed on the obtained Gaussian filtered image.

Figure 5:
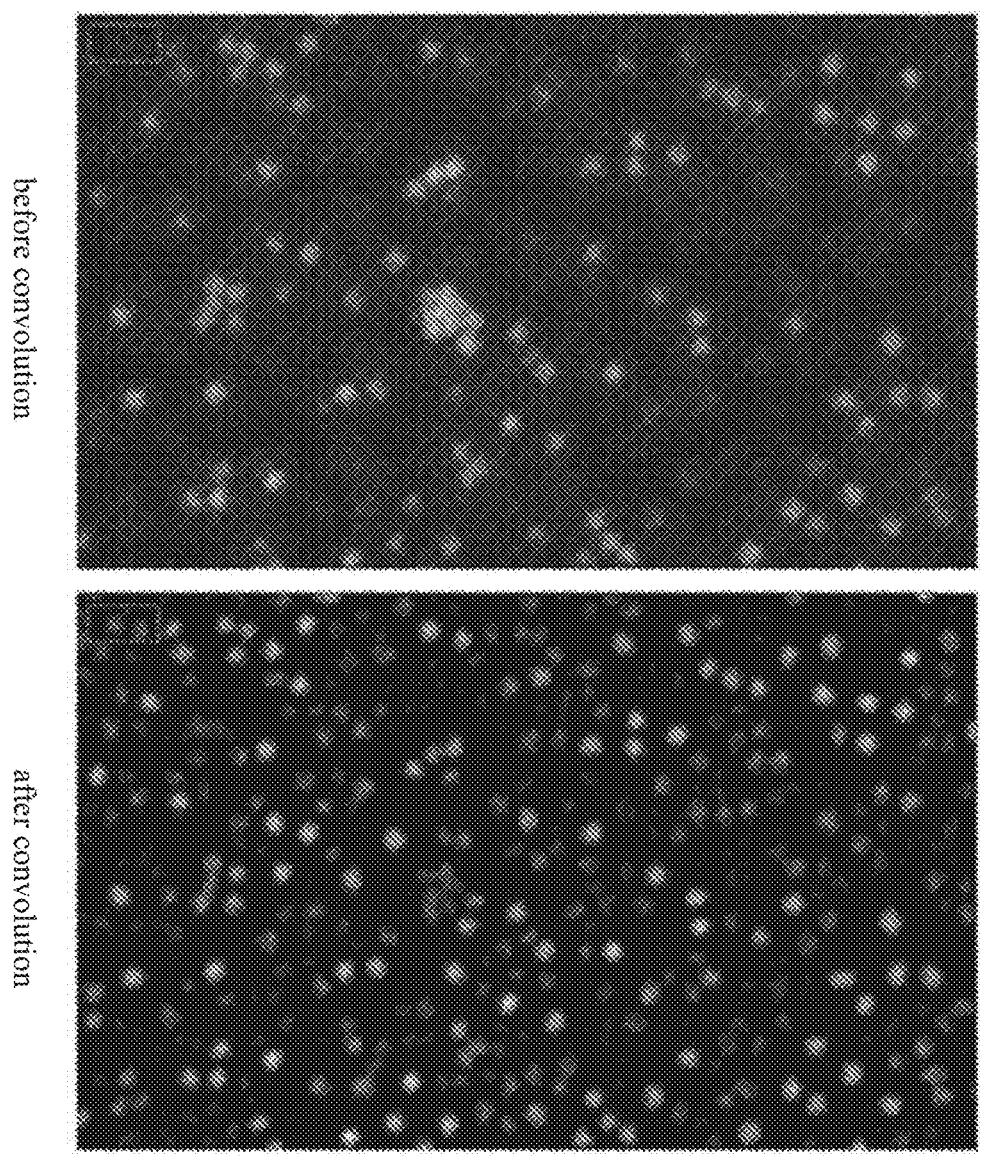
FIG. 5 shows comparison of an image before and after convolution according to an embodiment of the present application.

FIG. 5 shows a comparison of an image before and after convolution in the manner described above, the upper picture being the image before convolution and the lower picture being the image after convolution, and the boxes in the pictures illustrating the change in signal intensity and/or morphology of the same area in the image before and after convolution.

It will be appreciated that the size of the convolution kernel, the values in the convolution kernel and the value of n in, for example, Edge8Ints(x,y,n) may be adjusted, as required, for example, when the morphology and/or intensity changes of the target molecules across the image may have different characteristics, and for adjusting n, typically n=m/2 and is rounded down if the size of the ideal spot is known to be m*m.

For the settings of k3 and k4 or k5 and k6, similarly, the values of k3 and k4 or k5 and k6 are related to the density and distribution of the template molecules on the solid substrate and the imaging resolution, and it is generally desired that the size of k3×k4 or k5×k6 should be not smaller than the size of a target spot, which corresponds to a target signal or a target molecule or molecule cluster; preferably, it is also generally desired that the size of k3×k4 or k5×k6 should be smaller than the size of two independent spots on the image.

k3 and k4, or k5 and k6, may or may not be equal. Generally, the value ranges of k3, k4, k5 and k6 are all greater than 1 and less than 10.

In some embodiments, k3 is equal to k4, and/or k5 is equal to k6.

In some embodiments, k3 and k4 are both odd numbers greater than 1, and/or k5 and k6 are both odd numbers greater than 1. Further, for a platform with a target spot corresponding to a molecule cluster (for example, a template is amplified to form a molecule cluster), the molecule cluster is immobilized on a microsphere or a flowcell surface; typically, the size of the molecule cluster is hundreds of nanometers, and under the imaging optical path at a magnification of 20, k3 and k4 can both be odd numbers greater than 3, and/or k5 and k6 can both be odd numbers greater than 3. In this way, the calculation is facilitated, which is favorable for the construction of a spot set corresponding to the template and subsequent accurate basecalling.

S2 is related to the pixel of the converted image. For example, S2 may be determined based on all pixels of the converted image. In some embodiments, S2 is not less than a median of all pixels of the converted images sorted in ascending order of pixel values and/or not greater than the $80^{th}$ quantile of all pixels of the converted images sorted in ascending order of pixel values. In one example, the input image is converted into a 256-color bitmap (16-bit map), and S2 can be set to any value of 19-25. In this way, the spot can be effectively detected.

In one example, Gaussian filtering is performed on an original image, and then the convolution operation described above is performed to obtain a convolved image. All points (spots) with a peak value on the convolved image are then found out, and it is ensured that the peak value is greater than a specific value. For example, the specific value is set to be any value of 19-25; generally, the greater the peak value indicates a higher intensity, better-shaped spot; specifically, each pixel on the converted image has a midS, the value of the midS corresponding to the position of a bump is higher, and here 25 is set as a filtering threshold, and a position where the value of midS is greater than 25 is considered as a bump spot. Further, for all spots that meet the above conditions, the sub-pixel coordinates are determined on the original image using the 3×3 area centroid method.

In some embodiments, after the spots on the image are detected by using the method of any of the above examples, the detected spots are screened based on intensity of areas where the spots are located on the original image. In this way, relatively dark or particularly bright spots are removed or signals which are probably not or not simply from target molecules are removed, so that the calculation amount is reduced, and the proportion of high-quality reads is increased.

In still other embodiments, the spot detection comprises detecting each image of the set of images using a k7×k8 matrix, which comprises: determining that a k7×k8 matrix where a plurality of pixel values in designated directions show monotonic fluctuation corresponds to a candidate spot; and screening the candidate spot using pixels of at least a part of the area in a corresponding k7×k8 matrix to determine the spot, k7 and k8 being both natural numbers greater than 1, and the k7×k8 matrix comprising k7×k8 pixels.

Similarly, the values of k7 and k8 are generally related to the density and distribution of the template molecules on the solid substrate and the imaging resolution, and it is generally desired that the size of the k7×k8 matrix should be not smaller than the size of a target spot, which corresponds to a target signal or a target molecule or molecule cluster; preferably, it is also generally desired that the size of the k7×k8 matrix should be smaller than the size of two independent spots on the image.

In some examples, k7 is equal to k8, and/or k7 and k8 are both odd numbers greater than 1. In this way, the calculation is facilitated, which is favorable for the construction of a spot set corresponding to the template and subsequent basecalling.

The designated direction may be any direction from the center of the k7×k8 matrix, e.g., the central pixel or sub-pixel; the monotonic fluctuation refers to that pixel values of a plurality of pixels in a designated direction show no fluctuation, symmetrical fluctuation or approximately symmetrical fluctuation relative to the center of the k7×k8 matrix.

Figure 6:
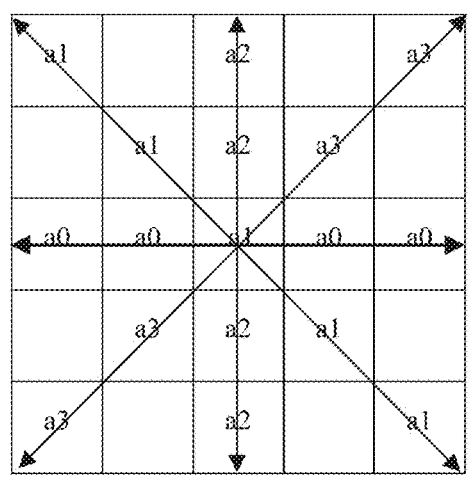
FIG. 6 shows a schematic diagram illustrating monotonic fluctuation of pixel values of a plurality of pixels in designated directions of a 5×5 matrix according to an embodiment of the present application.

In one example, referring to FIG. 6, FIG. 6 shows that the pixel values of a plurality of pixels in a designated direction of a 5×5 matrix show monotonic fluctuation. A specific designated direction may be a direction shown by any arrow, a0, a1, a2 and a3 indicate the pixel values of the pixels, and the matrix corresponds to a candidate spot.

Screening the candidate spot by using pixels of at least a part of the area in a corresponding k7×k8 matrix can further remove relatively dark or particularly bright spots or remove signals which are probably not or not simply from target molecules, so that the calculation amount is reduced, and the proportion of high-quality reads is increased.

For example, the average value or high frequency value of all pixels or pixels in any row or column in a k7×k8 matrix corresponding to a candidate spot is taken as the background, and the intensity of the center of the candidate spot is compared with the size of the background to screen the candidate spot; for example, the screening condition is set as that the intensity of the center of the candidate spot is not less than 3 times the background, and the candidate spot satisfying the condition is called a spot. In this way, the proportion of high-quality reads can be increased.

In some examples, the spot detection further comprises determining sub-pixel coordinates of the detected spot using a centroid method. In this way, coordinate information of the spot is obtained.

In a system that realizes imaging based on an optical system, generally chromatic aberration inevitably exists, and the chromatic aberration generally enables a static signal to have different positions in a plurality of images acquired at different time points; in addition, if the sequencing platform used performs multiple image acquisitions of one field of view on the flowcell based on the relative movement between the imaging system and the flowcell, the image acquisitions of the same field of view for different cycles of sequencing involve mechanical motion of the relevant structures, which generally also enables the signal to have different positions in the images acquired at different time points for the same field of view. Aligning the set of images can correct positional deviations due to the above-mentioned reasons at least to a certain extent.

In some embodiments, aligning the set of images comprises by taking a coordinate system of any image in the set of images, e.g., the first image, as a baseline, converting coordinate systems of the second image, the third image and the fourth image, so that the coordinate systems of the set of images are the same.

The method for converting the coordinate systems is not limited in this embodiment of the present application.

For example, the converting may be performed using correlation function in MatLab.

Specifically, in one cycle of sequencing, four images of one field of view come from four wavebands of two cameras. Although optical adjustment is performed as much as possible, pixel offset (chromatic aberration) still exists between the four images. Generally, if the optical setting is unchanged, offset caused by corresponding chromatic aberration can be considered to be fixed. If the set of images come from the first cycle of sequencing (cycle1) or the first several cycles of sequencing, generally there's no crosstalk or insignificant crosstalk between two designated ones of the four signals corresponding to the four types of bases in the cycle1 or the first several cycles of sequencing. For example, A, T, G and C carry fluorescent dyes ATTO-532, ROX, CY5 and IF700, respectively, and in any of the first several cycles of sequencing, at one time point, the first camera photographs A and the second camera photographs G at the same time, and at another time point, the first camera photographs T and the second camera photographs C at the same time; according to the images or signals acquired in that cycle, generally there's crosstalk between the A and T signals or between the G and C signals, but there's no crosstalk or insignificant crosstalk between the C and T signals or between the A and G signals; with regard to no crosstalk or insignificant crosstalk between the C and T signals, it is shown as that the T signal will not be acquired in a certain position when the C signal is acquired there (T is not bright when C is bright), and thus, in a certain sequencing, it is generally difficult to determine the fixed offset with images from one cycle of the first several cycles of sequencing.

Thus, in some examples, aligning the set of images comprises performing the aligning using images from cycle M of sequencing. M is, for example, greater than 20, 30 or 50. One cycle of sequencing usually can determine the base type of one position in the template. When the sequencing proceeds to cycle M, for example, cycle 20, 50, 80, 100 or 150, crosstalk due to partial overlapping of emission spectra of fluorescent dyes and/or phasing due to asynchronous chemical reactions are generally obvious because of accumulation, superposition or the like, which is shown as that signals of four types of bases have crosstalk between every two. Images acquired in the cycle M can be used for determining offset, and thereby the set of images are aligned.

In some examples, the images from the cycle M of sequencing comprise a fifth image, a sixth image, a seventh image and an eighth image. The fifth image, the sixth image, the seventh image and the eighth image correspond to the same type of nucleotide as the first image, the second image, the third image and the fourth image, respectively, in the set of images.

In one example, a set of images for constructing the spot set corresponding to the template are also from the cycle M, and the fifth image, the sixth image, the seventh image and the eighth image are the same as the first image, the second image, the third image and the fourth image, respectively, in the set of images.

In one example, the set of images are from cycle1, and the offset is determined using the images from cycle 100 of the same field of view to align the set of images. Specifically, for example, coordinate systems of the sixth image, the seventh image and the eighth image are converted by taking a coordinate system of the fifth image as a baseline, which may comprise: dividing the fifth image and the sixth image separately into a group of blocks with the size of k9×k10 in the same way, k9 and k10 being both natural numbers greater than 30, and k9×k10 comprising k9×k10 pixels; determining an offset of each block of the sixth image relative to a corresponding block of the fifth image; and aligning the second image and the first image based on the offset. Similarly, the third image and the first image, and the fourth image and the first image, are aligned to quickly and accurately realize the aligning of the set of images.

k9 and k10 may or may not be equal. The values of k9 and k10 are limited by the distribution, density and imaging resolution of the target molecules or molecule clusters on the detection area, and it is expected that the number of spots present on a k9×k10 block is statistically significant, e.g., greater than 30, 50, 100 or 500.

Assuming that the offset of the images of a particular field of view in one cycle of sequencing due to chromatic aberration is fixed, it can be understood that, as long as there is signal crosstalk between every two images in one cycle of sequencing for the field of view, the images of this cycle of sequencing can be used to determine the fixed offset regardless of the form of the signals with crosstalk on the images, thus aligning the set of images for constructing the spot set corresponding to the template. In some instances, grid signals regularly distributed in the horizontal and vertical directions may be set on different detection areas, e.g., different flowcells, or the same detection area, as feature information (information source), which can be imaged on different channels or wavebands, that is, can be acquired no matter which base signal is acquired, and it is easy to align the images using the feature information, including its distribution rule. After the image is divided into a plurality of blocks, by aligning the feature information, the offset of each corresponding set of blocks can be determined.

The image is divided into blocks, and adjacent blocks may or may not overlap. In one example, adjacent blocks do not overlap and there is a common edge or vertex between adjacent blocks.

Figure 7:
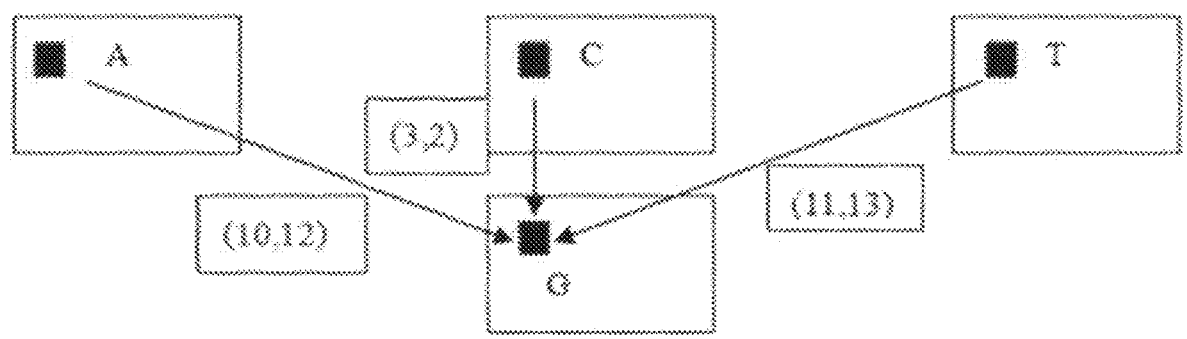
FIG. 7 shows a process of dividing an image into a plurality of blocks and determining an offset between the blocks to align images from one cycle of sequencing for a field of view according to an embodiment of the present application.

FIG. 7 illustrates a process of dividing an image into a plurality of blocks and determining an offset between the blocks to align images from one cycle of sequencing for a field of view in one embodiment. A black square on the figure represents a block, and specifically, by taking a coordinate system of a block on the image corresponding to base G (G image for short) as a baseline or reference, the offset of a corresponding block on each of A image, C image and T image relative to the block on the G image is determined.

Figure 8:
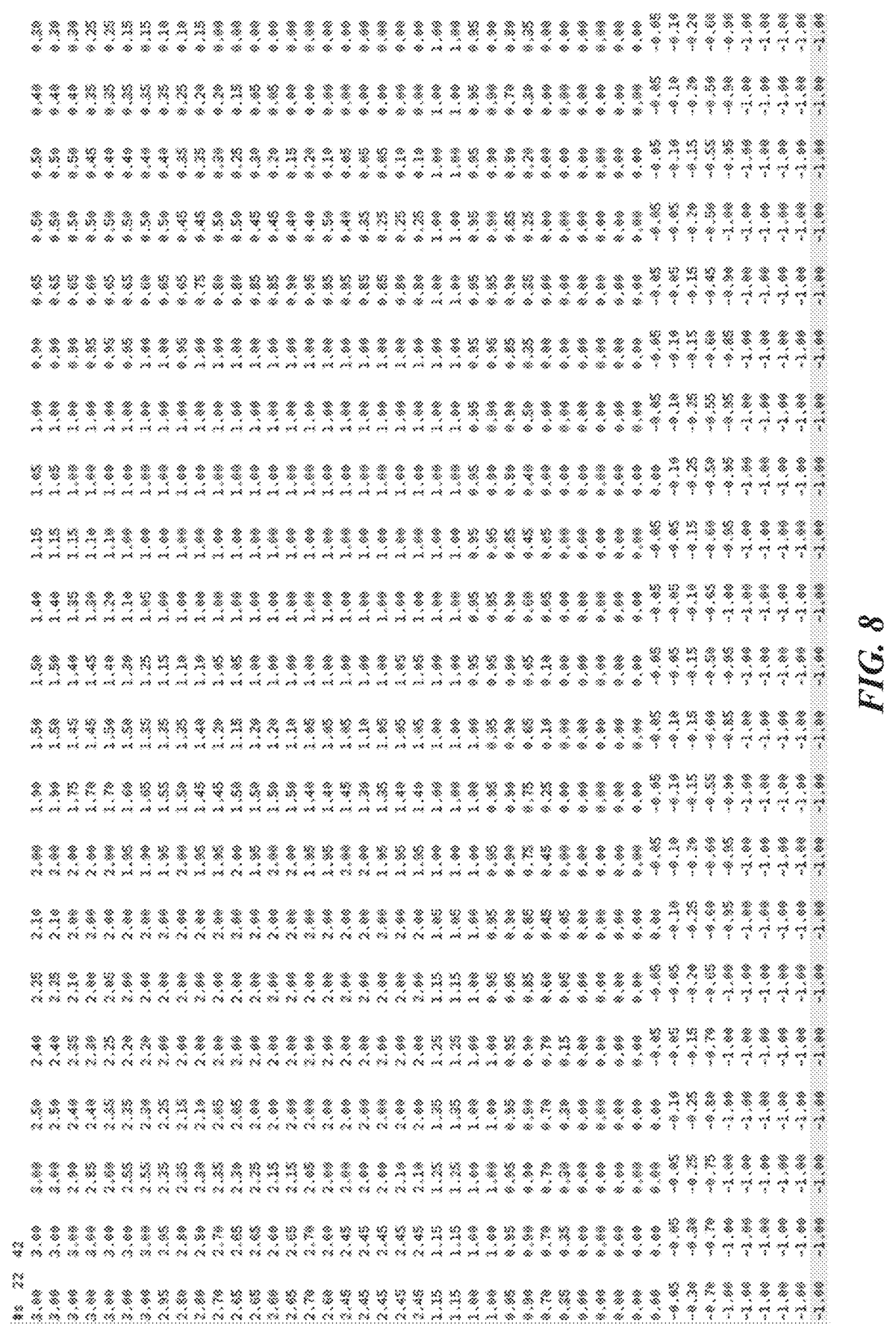

In tests, it is found that the offsets between corresponding blocks are not fixed; that is, the offsets of combinations of two blocks located at different positions on images are different. For example, the offset of two blocks located in the central areas of two images are 5 pixels, and the offset of two blocks located in the edge areas of two images are 10 pixels; in addition, the difference in the offset of adjacent combinations of blocks is small. For example, for an 4112×2176 image, the offset in the long edge 4112 is 4-5 pixels, and the offset in the short edge 2176 is approximately 2-3 pixels. In one example, k9=k10=100, and the offset may be considered generally constant within a 100×100 block. FIG. 8 illustrates at least a part of the offsets of combinations of two corresponding blocks after dividing the two images into 100×100 blocks, and the offset table illustrated in FIG. 8 may represent the coordinate system relationship between the two images.

In some embodiments, merging the spots on the aligned set of images comprises merging a plurality of spots within a preset range k11×k12 into one spot, k11 and k12 being both natural numbers greater than 1, and k11×k12 comprising k11×k12 pixels.

Generally, k11×k12 is set to be no greater than the size of two separate target spots, and preferably k11×12 is set to be no greater than the size of one target spot.

In a certain imaging system, for example, the size of the electronic sensor is 6.5 µm, the microscope magnification is 60×, the resolution is 0.1 µm, and the size of a spot corresponding to a target molecule (including a molecule cluster) is generally less than 10×10 or 5×5. It may be set that k11=k12=3; namely, the preset range is set to be 3×3 for merging the spots, so that the spot set corresponding to the template can be accurately constructed.

Specifically, when merging the spots within the preset range, a blank set or blank image or blank template (TemplateVec) may be set first, and then the spots on the first image, the second image, the third image or the fourth image (A image, C image, G image and T image for short) are sequentially marked on the blank image. When a certain spot is marked, if it is found that there is already a spot in its adjacent position (within the preset range), weighing can be performed based on the intensity of the two spots, thus determining the position of the new spot obtained after merging the two spots. For example, the intensity of spot 1 is 350 and its coordinates are (3.0, 5.0), and the intensity of spot 2 is 150 and its coordinates are (4.0, 7.0); the two spots are marked as a new spot, and the intensity of the new spot is 290, and its coordinates are (3.3, 5.6). In this way, the merging of the spots which meet the preset condition on the set of images is realized, which is favorable for obtaining the spot set corresponding to the template.

Figure 9:
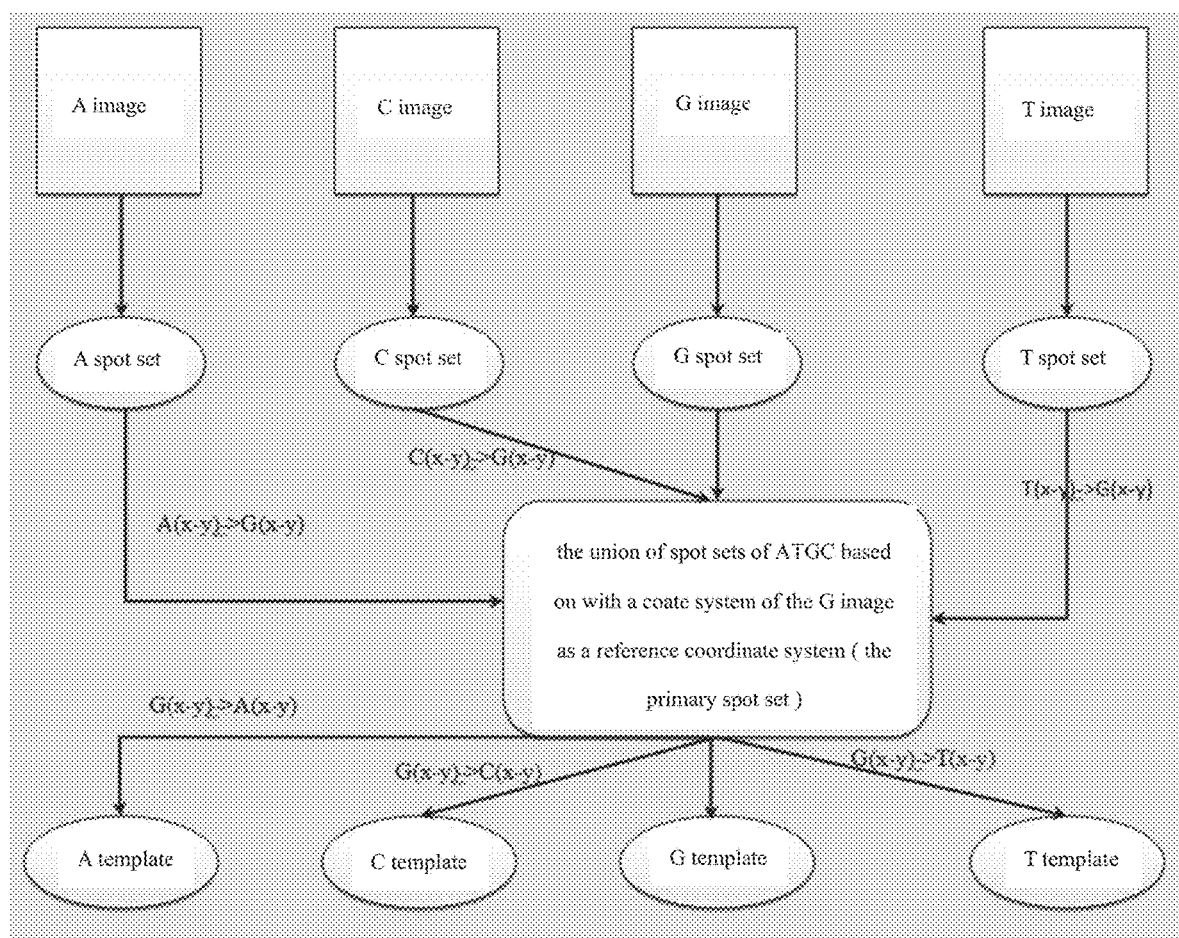
FIG. 9 shows a process of constructing a spot set corresponding to a template with a set of images from one cycle of sequencing according to an embodiment of the present application.

Referring to FIG. 9, FIG. 9 illustrates a process of constructing a spot set corresponding to a template with a set of images from one cycle of sequencing in an embodiment, which comprises detecting and identifying spots on an A image, a C image, a G image and a T image in the set of images to obtain a spot set of each image, aligning the set of images with a coordinate system of the G image as a reference coordinate system (including merging the spot sets of the images) to obtain a primary spot set, and performing coordination system conversion to convert a coordinate system of the primary spot set into original coordinate systems of the A image, the C image, the G image and the T image, thus obtaining the spot set corresponding to four types of nucleotides or bases, i.e., obtaining the template of four types of nucleotides or bases.

In this embodiment, the intensity in S21 is corrected intensity. In some embodiments, the intensity correction comprises crosstalk correction and/or phase correction.

Specifically, the image to be detected is aligned to the spot set corresponding to the template before the intensity of the corresponding coordinate position on the image to be detected is corrected. In this way, the subsequent steps are facilitated.

Figure 10:
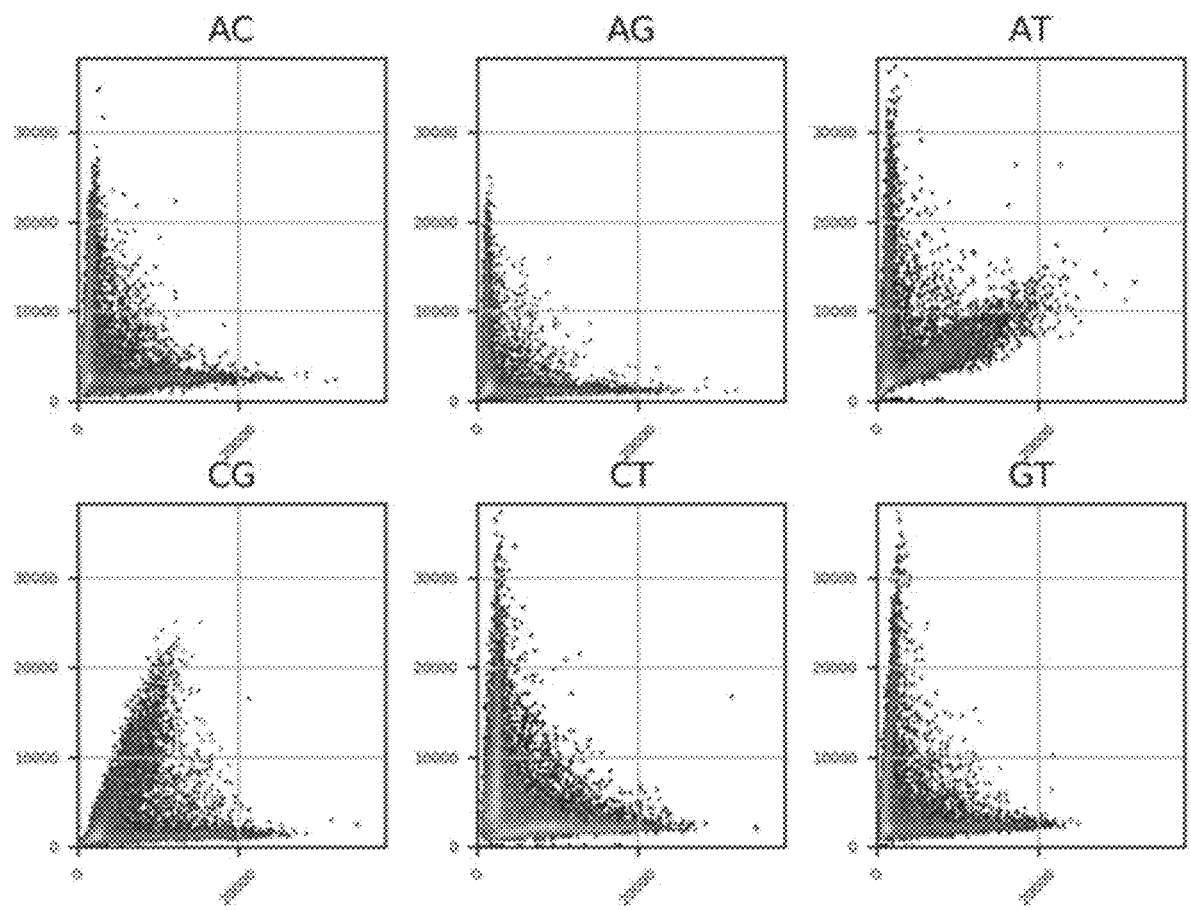
FIG. 10 shows crosstalk scatter diagrams between every two of four images of a field of view according to an embodiment of the present application.

In one example, A, T, G and C carry fluorescent dyes ATTO-532, ROX, CY5 and IF700, respectively, and in sequencing, the four fluorescent dyes are excited by lasers with two wavebands, and after each excitation, two cameras are used for simultaneously acquiring fluorescent signals; FIG. 10 shows crosstalk diagrams between every two of four images of one field of view in cycle 50 of sequencing based on the example. From the top to the bottom and then from left to right, the diagrams are a bases A-C crosstalk scatter diagram (abscissa is relative intensity of A signal, and ordinate is relative intensity of C signal), a bases A-G crosstalk scatter diagram (abscissa is relative intensity of A signal, and ordinate is relative intensity of G signal), a bases A-T crosstalk scatter diagram (abscissa is relative intensity of A signal, and ordinate is relative intensity of T signal), a base C-G cross talk scatter plot (abscissa is relative intensity of C signal, ordinate is relative intensity of G signal), a bases C-T crosstalk scatter diagram (abscissa is relative intensity of C signal, and ordinate is relative intensity of T signal), and a bases G-T crosstalk scatter diagram (abscissa is relative intensity of G signal, and ordinate is relative intensity of T signal), one spot on each scatter diagram representing a position of corresponding coordinates on the image to be detected; as can be seen from the two axes of each crosstalk scatter diagram and the dispersion condition of the spots on the diagrams, the crosstalk of the A signal (A image) by the T signal is obvious, and the crosstalk of the C signal (C image) by the G signal is obvious, which is shown as that multiple positions of corresponding coordinates on the A image have relatively obvious T signals, and multiple positions of corresponding coordinates on the C image have relatively obvious G signals.

In some examples, the intensity correction comprises crosstalk correction, which is performed based on at least one of images from the same cycle of sequencing and same field of view and corresponding to different types of nucleotides or bases.

Crosstalk correction is favorable for accurate basecalling. In some examples, an image Xi and the image to be detected are from the same cycle of sequencing, the image Xi and the image to be detected correspond to the same field of view, the image to be detected is subjected to crosstalk by signals of a nucleotide corresponding to the image Xi, and the crosstalk correction of the image to be detected comprises: fitting signals of positions of a plurality of corresponding coordinates in a specific area of the image to be detected to obtain a fitting result, and correcting the signals of the positions of the corresponding coordinates on the image to be detected based on the fitting result. In this way, the signal crosstalk from the base corresponding to the image Xi on the image to be detected can be eliminated, so that the signals in the image to be detected only correspond to one base as much as possible, which is favorable for accurate basecalling and accurate determination of the nucleotide sequence. Unless otherwise stated, "AC correction" or "A→C" or "A-C" represents correcting the crosstalk of the A signal at positions of corresponding coordinates of the C image (i.e., correcting the crosstalk of the A signal to the C signal); similarly, "TA correction" or "T→A" represents correcting the crosstalk of the T signal at positions of corresponding coordinates of the A image (i.e., correcting the crosstalk of the T signal to the A signal), "CG correction" or "C→G" represents correcting the crosstalk of the C signal at positions of corresponding coordinates of the G image (i.e., correcting the crosstalk of the C signal to the G signal), and so on.

The four-dimensional data are subjected to correction in pairs, and there are 12 cases. The correction process can be expressed as $$\begin{pmatrix} R_{AA} & R_{CA} & R_{GA} & R_{TA} \\ R_{AC} & R_{CC} & R_{GC} & R_{TA} \\ R_{AG} & R_{CG} & R_{GG} & R_{TG} \\ R_{AT} & R_{CT} & R_{GT} & R_{TT} \end{pmatrix} \begin{pmatrix} I_A \\ I_C \\ I_G \\ I_T \end{pmatrix} = \begin{pmatrix} I'_A \\ I'_C \\ I'_G \\ I'_T \end{pmatrix},$$

in which $$\begin{pmatrix} R_{AA} & R_{CA} & R_{GA} & R_{TA} \\ R_{AC} & R_{CC} & R_{GC} & R_{TA} \\ R_{AG} & R_{CG} & R_{GG} & R_{TG} \\ R_{AT} & R_{CT} & R_{GT} & R_{TT} \end{pmatrix}$$

is a crosstalk correction coefficient matrix, and values in the crosstalk matrix represent fitting results (correction coefficients) of the signal pairs; for example, $R_{AC}$ represents the fitting result or correction coefficient based on which the crosstalk of the A signal at positions of corresponding coordinates of the C image is corrected;

$$\begin{pmatrix} I_A \\ I_C \\ I_G \\ I_T \end{pmatrix}$$

are observed values $$\begin{pmatrix} I'_A \\ I'_C \\ I'_G \\ I'_T \end{pmatrix}$$

and are real values (corrected values).

Figure 11:
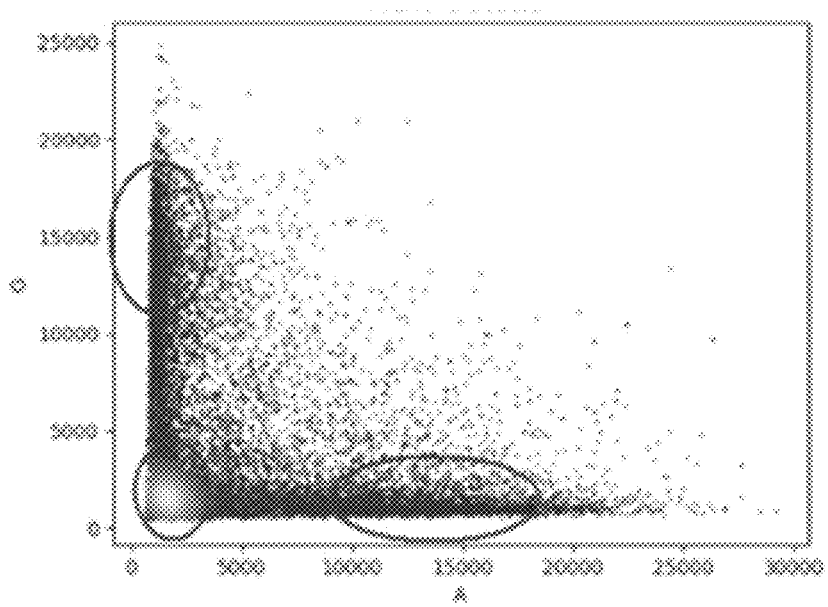
FIG. 11 shows an A-G crosstalk scatter diagram, with the abscissa being A and the ordinate being G, according to an embodiment of the present application.

The specific area may be the entire image to be detected or a part of the image to be detected. Preferably, the specific area is selected from at least a part of a central area of the image to be detected. A central area of an image may be sized as generally understood; for example, for an image of 4000×2000, the central area of the image may be 3000× 1500, 2056×1024, 2000×1500, 1024×1024, 1024×512, 1000×500, 1000×1000, 512×512, 512×256, or the like, while the other area of the image may be referred to as an edge area. Generally, the intensity value fluctuation at positions of corresponding coordinates in the central area of the image is small, which is shown as the spots being more convergent on the crosstalk diagram, such as the spots in the black circles in the A-G crosstalk scatter diagram illustrated in FIG. 11. The fitting result or correction coefficient determined by fitting the intensity values of at least a part of the positions in this area is used for correction, so that the chromatic aberration correction can be quickly and accurately realized.

The method for fitting is not limited in this embodiment; for example, the fitting may be performed using softwares such as MatLab cftool kit, aTool and CurveExpert; the fitting may be linear fitting or non-linear fitting. The amount of data or samples used for fitting, i.e., how many intensity values of the positions of corresponding coordinates within a particular area on the image are selected for the fitting, is not particularly limited, and in principle, it is sufficient if Y coefficients of the equation with Y unknowns to be fitted can be solved. For example, for linear fitting, 2, 5, 10, 20, 30, or 50 intensity values may be used; preferably, it is desired that the amount of samples should be statistically significant, such as not less than 20, 30 or 50; optionally, in order to prevent the calculation amount from being too large, the amount of samples may be limited to less than 200 or less than 100 at the same time. In this way, correction can be accurately achieved using the corresponding fitting result (correction coefficient).

In some examples, linear fitting is performed. In this way, the calculation is facilitated and time is saved, which is favorable for quick correction.

Figure 12:
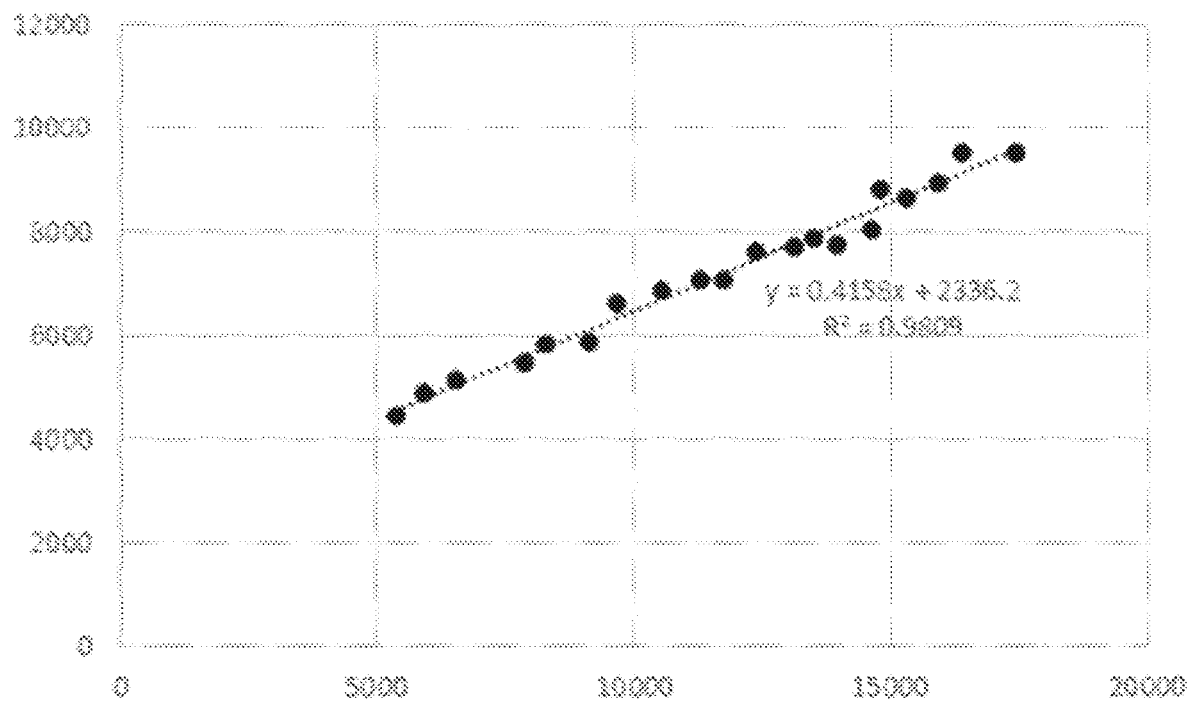
FIG. 12 shows a fitted curve of the A-T signal intensity according to an embodiment of the present application.
Figure 13:
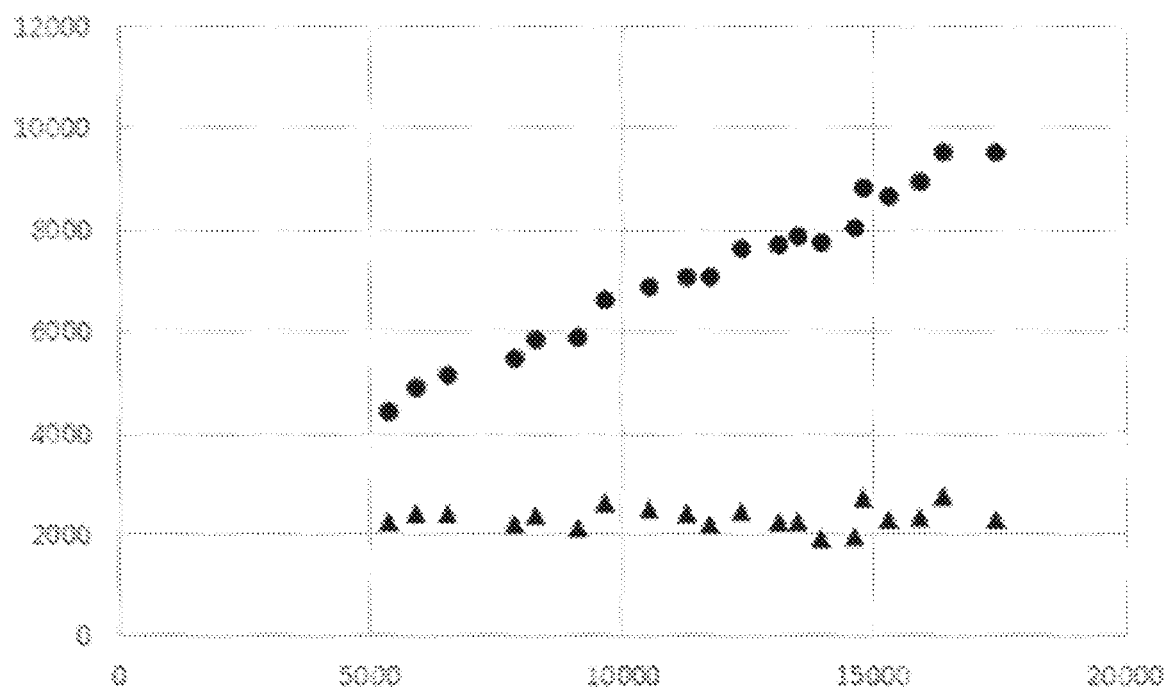
FIG. 13 shows the results of the A-T signal intensity before and after correction according to an embodiment of the present application.

Specifically, referring to FIG. 12 and FIG. 13. In one example, the image to be detected is A image, and the image Xi is T image. The intensity values of the signals at the positions of 20 corresponding coordinates of the central area on the image to be detected are selected for linear fitting, and FIG. 12 shows the result of the fitting, the abscissa being the relative signal intensity value of A, and the ordinate being the relative signal intensity value of T. The result of the fitting determines the slope k of the fitted straight line, and the slope is used as a correction coefficient to correct the intensity of the signal at the position of each corresponding coordinate of the image to be detected; for example, $I_T = I_T - I_A \times k$, in which $I_T$ is the T signal intensity at the position after correction, $I_T$ is the T signal intensity observed at the position (observed value), and $I_A$ is the A signal intensity observed at the position (observed value). FIG. 13 illustrates the results, before correction and after correction by this method, of the signals at the positions of the 20 corresponding coordinates on the image to be detected. In this way, the contribution of the T signal to the fluctuation of the signal intensity at the position of the corresponding coordinates of the image to be detected can be eliminated or reduced, and the corrected image to be detected can be obtained.

Figure 14:
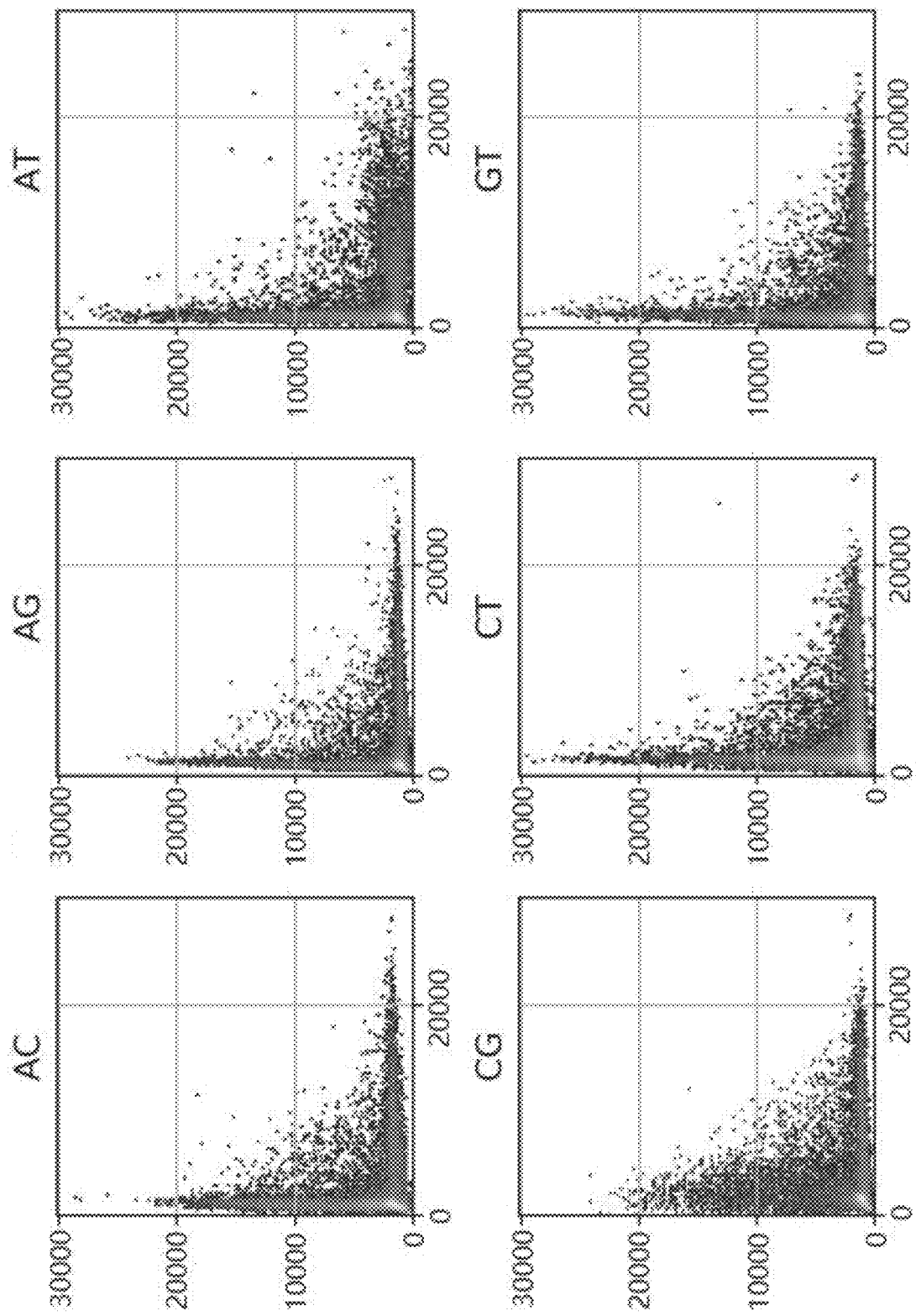
FIG. 14 shows crosstalk diagrams between every two of four images from one cycle of sequencing for a field of view after chromatic aberration correction according to an embodiment of the present application.

In comparison to FIG. 10, FIG. 14 shows crosstalk diagrams between every two of four images of the same field of view in this cycle of sequencing after chromatic aberration correction is performed by the method as described above. It can be seen that, through the chromatic aberration correction, the signal crosstalk between the images corresponding to different bases in the same cycle of sequencing for the same visual field is significantly reduced, which is favorable for accurate basecalling and the obtaining of longer sequences.

Figure 15:
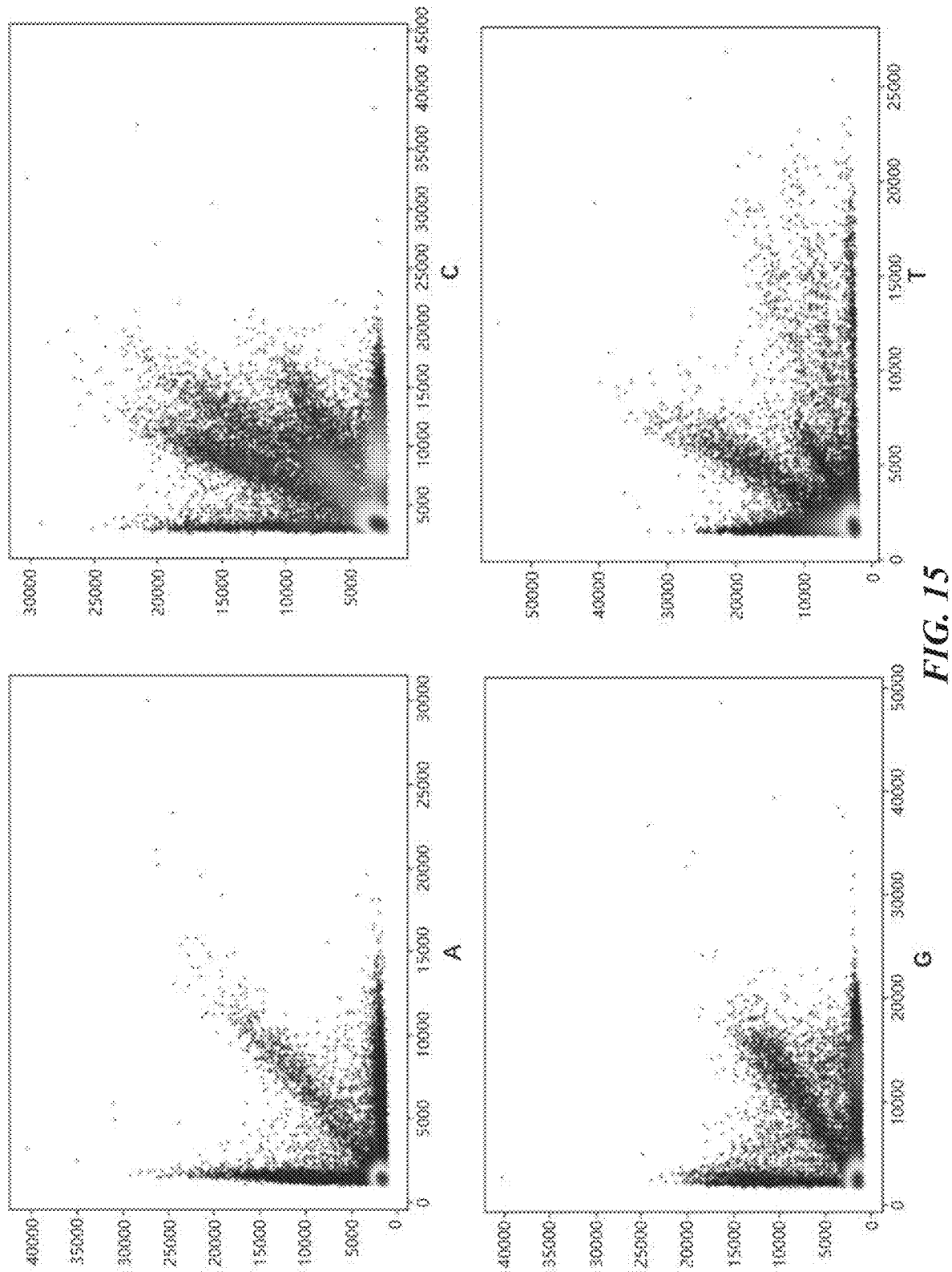
FIG. 15 shows signal crosstalk diagrams for specific bases from cycle1 and cycle2 for a field of view according to an embodiment of the present application; from top to bottom and then from left to right, the diagrams are phasing scatter diagrams of A, C, G and T, respectively, and in each phasing scatter diagram, the abscissa is the relative signal intensity of the base from cycle1, and the ordinate is the relative signal intensity of the same base from cycle2.
Figure 16:
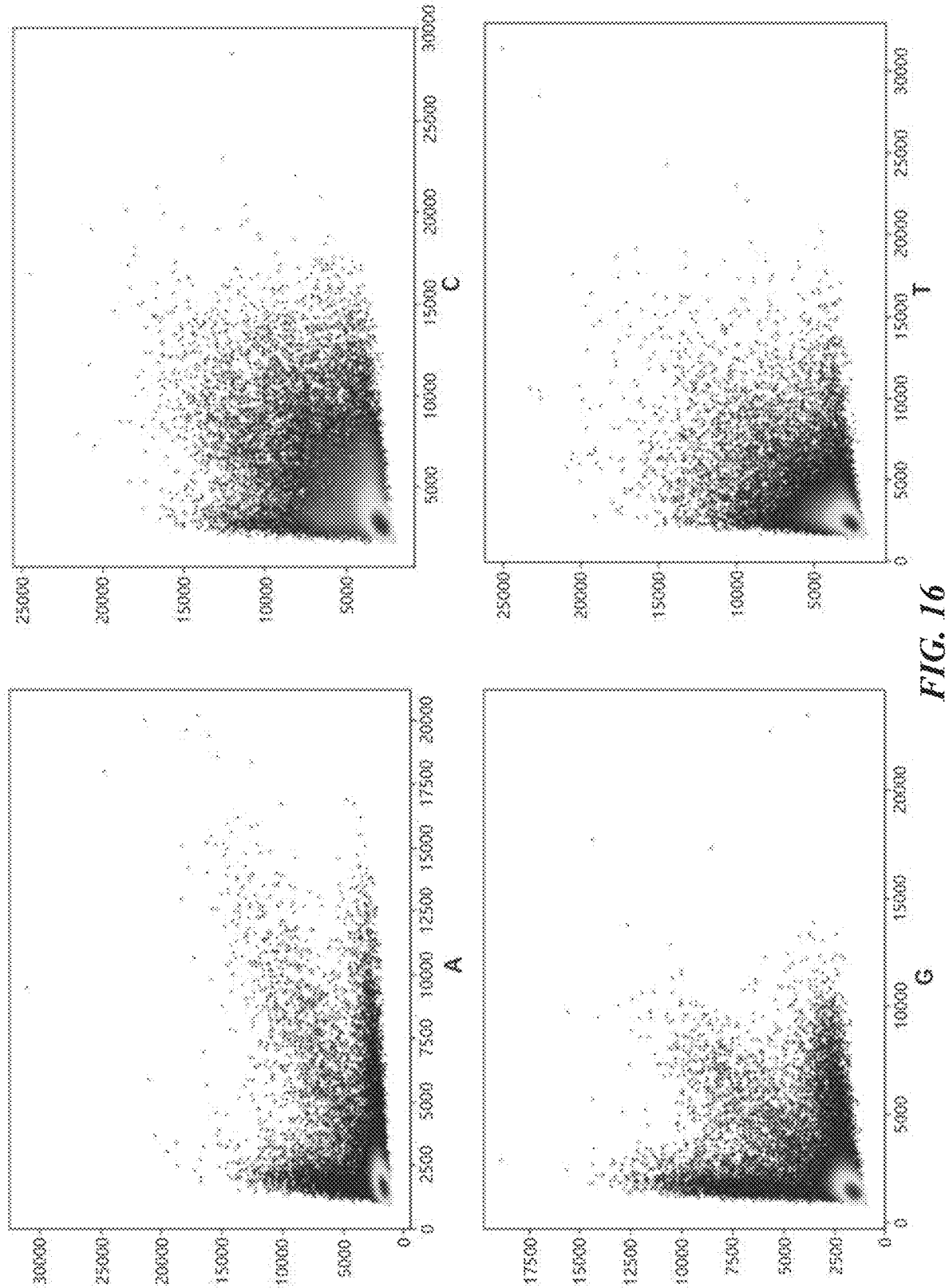
FIG. 16 shows signal crosstalk diagrams for specific bases from cycle30 and cycle31 for a field of view according to an embodiment of the present application; from top to bottom and then from left to right, the diagrams are phasing scatter diagrams of A, C, G and T, respectively, and in each phasing scatter diagram, the abscissa is the relative signal intensity of the base from cycle30, and the ordinate is the relative signal intensity of the same base from cycle31.
Figure 17:
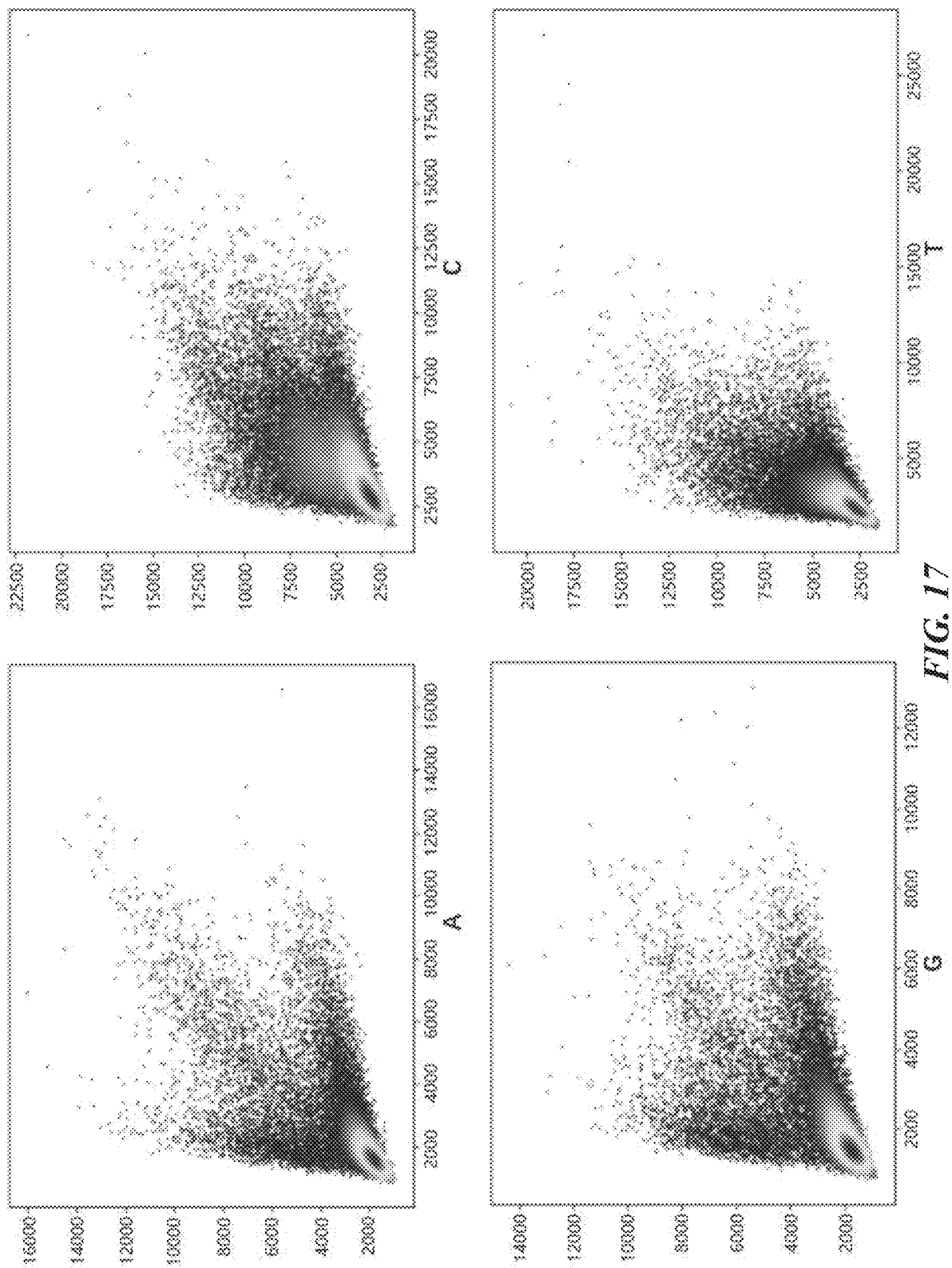
FIG. 17 shows signal crosstalk diagrams for specific bases from cycle60 and cycle61 for a field of view according to an embodiment of the present application; from top to bottom and then from left to right, the diagrams are phasing scatter diagrams of A, C, G and T, respectively, and in each phasing scatter diagram, the abscissa is the relative signal intensity of the base from cycle60, and the ordinate is the relative signal intensity of the same base from cycle61.
Figure 18:
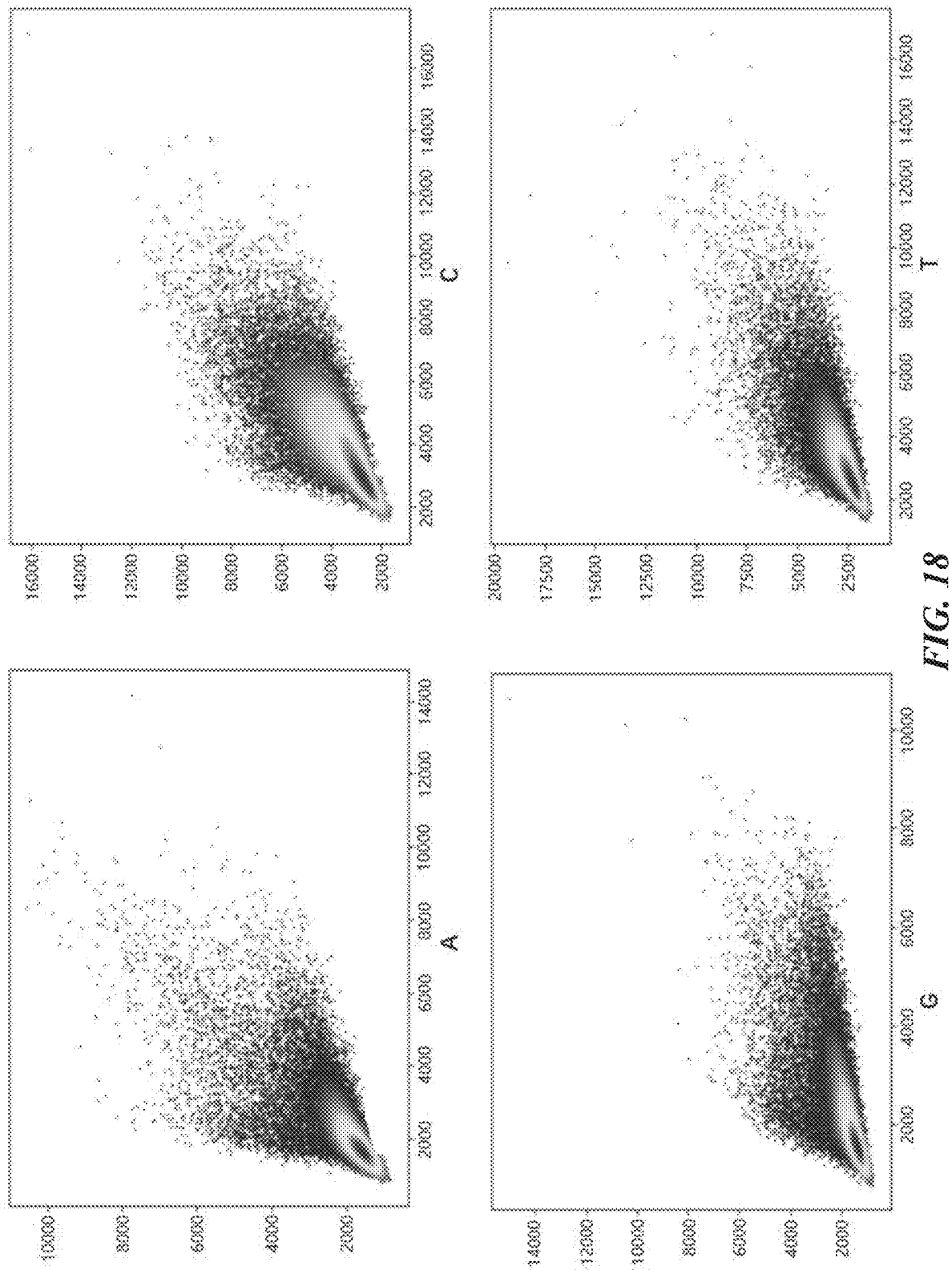
FIG. 18 shows signal crosstalk diagrams for specific bases from cycle90 and cycle91 for a field of view according to an embodiment of the present application; from top to bottom and then from left to right, the diagrams are phasing scatter diagrams of A, C, G and T, respectively, and in each phasing scatter diagram, the abscissa is the relative signal intensity of the base from cycle90, and the ordinate is the relative signal intensity of the same base from cycle91.

Referring to FIGS. 15-18, FIGS. 15-18 show diagrams of signal crosstalk between two images corresponding to the same base from adjacent cycles of sequencing for the same field of view in one example, a spot on the diagrams represents the position of corresponding coordinates, and the abscissa and ordinate are both relative signal intensity; from top to bottom and then from left to right, the four phasing scatter diagrams in FIG. 15 are the signal intensity relationship diagrams of the two A images, the two C images, the two G images and the two T images of cycle1 and cycle2, respectively; the four phasing scatter diagrams in FIG. 16 are the signal intensity relationship diagrams of the two A images, the two C images, the two G images and the two T images of cycle30 and cycle31, respectively; the four phasing scatter diagrams in FIG. 17 are the signal intensity relationship diagrams of the two A images, the two C images, the two G images and the two T images of cycle60 and cycle61, respectively; and the four phasing scatter diagrams in FIG. 18 are the signal intensity relationship diagrams of the two A images, the two C images, the two G images and the two T images of cycle90 and cycle91, respectively.

It can be seen that in this example, the phase unbalance (phasing or prephasing) of C or T is obvious relative to A or G; and as the number of sequencing cycles increases, the signal crosstalk caused by the phase unbalance of the chemical reaction of various bases is more serious. As can be seen from FIG. 18, when the sequencing proceeds to cycle91 in this example, the phase unbalance already makes it difficult to accurately distinguish whether the signal at a certain position in the T image comes from the cycle90 of sequencing or the cycle91 of sequencing. Generally, when the sequencing proceeds to the end, there will be the case where the positions of all corresponding coordinates are bright and have uniform brightness, and in such a case, the correct bases cannot be called, and that is, the sequencing cannot be continued. phase unbalance is a main reason for limiting the read length of sequencing by synthesis.

Figure 19:
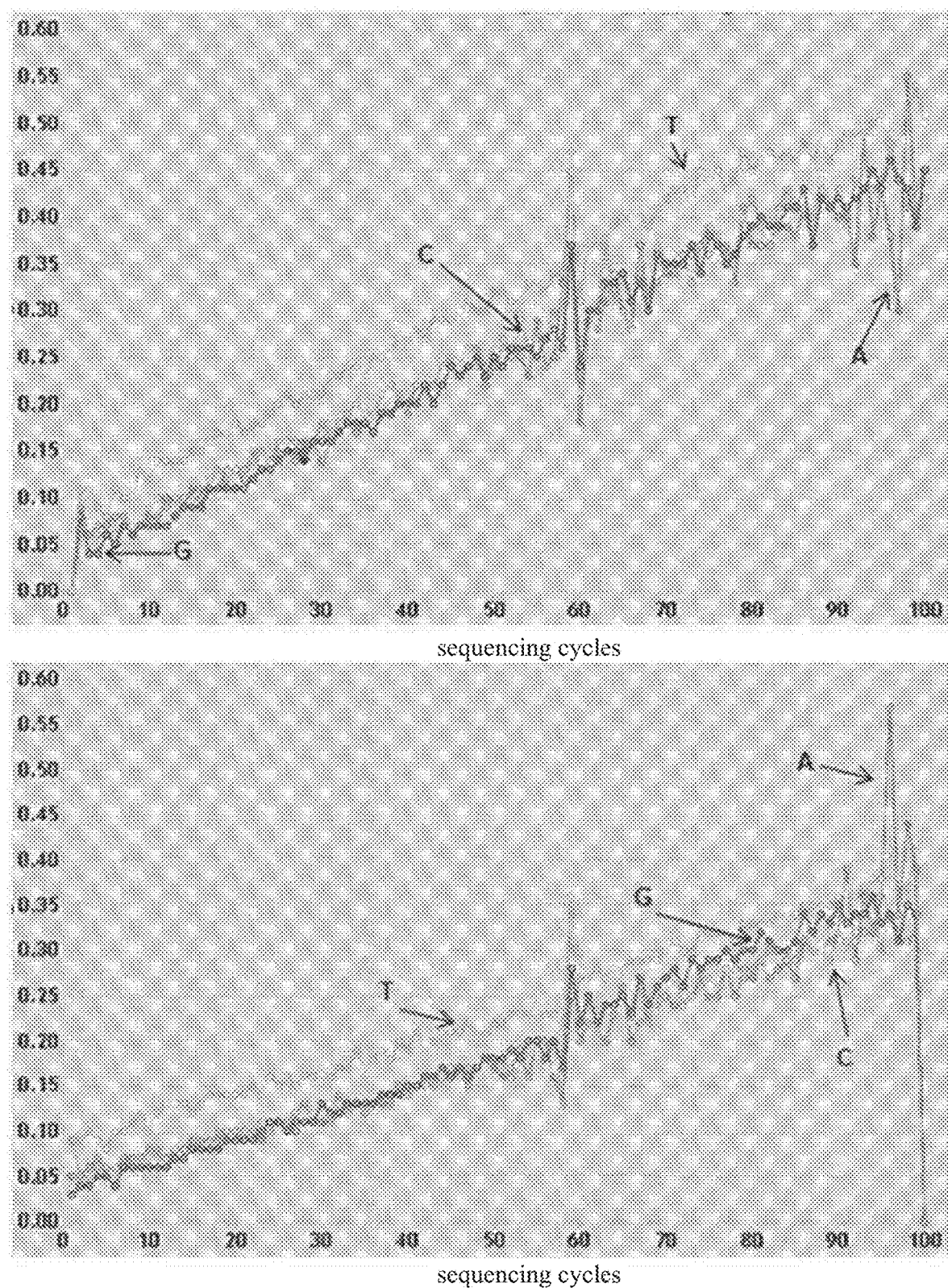
FIG. 19 shows the relationship between the phasing proportion or the prephasing proportion of four types of bases and the number of sequencing cycles according to an embodiment of the present application, with the abscissa being the number of sequencing cycles and the ordinate being the prephasing proportion.

The upper and lower graphs in FIG. 19 show the relationship between the phasing proportion or the prephasing proportion of four types of bases in sequencing of a certain nucleic acid sample and the number of sequencing cycles, and as the number of sequencing cycles increases, the phasing proportion and the prephasing proportion of each base both increase.

Phasing or prephasing correction is favorable for correct basecalling and the obtaining of longer sequences. The phase correction can be performed before or after the crosstalk correction.

In some examples, the intensity correction comprises phase correction, which is performed based on at least one of images from adjacent cycles of sequencing and corresponding to the same type of nucleotide. Specifically, in one example, an image Yj and the image to be detected are from two adjacent cycles of sequencing (e.g., the image Yj is from cycle31 of sequencing, and the image to be detected is from cycle30 of sequencing), the image Yj and the image to be detected correspond to the same field of view, the image Yj and the image to be detected correspond to the same type of nucleotide or base (e.g., A), and the phase correction comprises: fitting signals of positions of a plurality of corresponding coordinates in a specific area of the image to be detected to obtain a fitting result, and correcting the signals of the positions of the corresponding coordinates on the image to be detected based on the fitting result.

Figure 20:
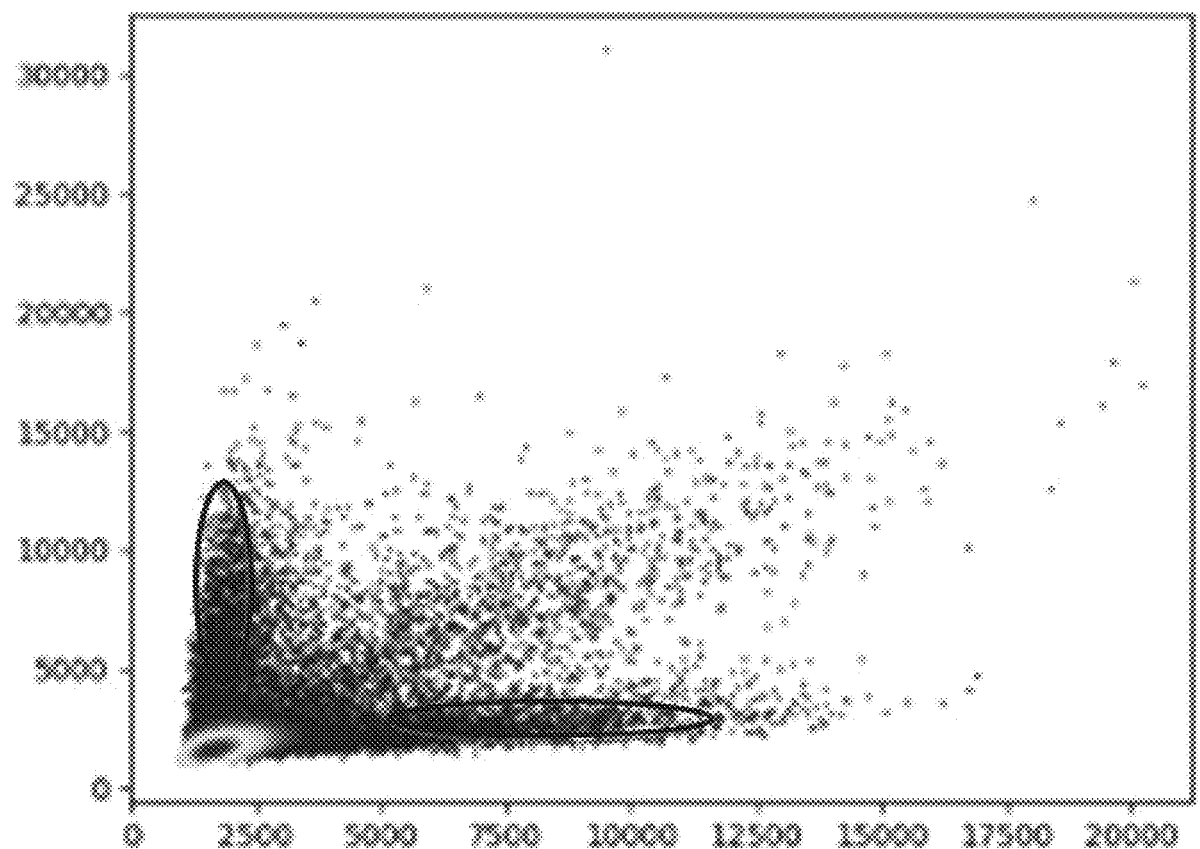
FIG. 20 shows the phasing scatter diagram of A for cycle30 and cycle31 according to an embodiment of the present application.

Similarly, the specific area here may be the entire image to be detected or a part of the image to be detected. Preferably, the specific area is selected from at least a part of a central area of the image to be detected. A central area of an image may be sized as generally understood; for example, for an image of 4000×2000, the central area of the image may be 3000×1500, 2056×1024, 2000×1500, 1024×1024, 1024×512, 1000×500, 1000×1000, 512×512, 512×256, or the like, while the other area of the image may be referred to as an edge area. Generally, the intensity value fluctuation at positions of corresponding coordinates in the central area of the image is small, which is shown as the spots being more convergent on the phasing scatter diagram, such as the spots in the black circles in the phasing scatter diagram of the A image from cycles 30 and 31 illustrated in FIG. 20. The fitting result or correction coefficient determined by fitting the intensity values of at least a part of the positions in this area is used for correction, so that the phase correction can be quickly and accurately realized.

Similarly, the method for fitting is not limited in this embodiment; the fitting may be linear fitting or non-linear fitting. The amount of data or samples used for fitting, i.e., how many intensity values of the positions of corresponding coordinates within a particular area on the image are selected for the fitting, is not particularly limited, and in principle, it is sufficient if Y coefficients of the equation with Y unknowns to be fitted can be solved. For example, for linear fitting, 2, 5, 10, 20, 30, or 50 intensity values may be used; preferably, it is desired that the amount of samples should be statistically significant, such as not less than 20, 30 or 50; optionally, in order to prevent the calculation amount from being too large, the amount of samples may be limited to less than 200 or less than 100 at the same time. In this way, correction can be accurately achieved using the corresponding fitting result (correction coefficient).

In some examples, linear fitting is performed using the method described in the example above to correct phasing before crosstalk correction, and $R^2=0.97$ for the linear fitting; in some other examples, signals at the same multiple positions are used for fitting, and linear fitting is performed using the method described in the example above to correct phasing after crosstalk correction, and $R^2=0.93$ for the linear fitting.

For S31, in some examples, the intensity of the signal at a position of the corresponding coordinates on the image to be detected is as an array containing four values (four-dimensional data) corresponding to signal intensity of four types of nucleotides or bases at that position, which, for example, can be expressed as {Ints A, Ints T, Ints G, Ints C}, Ints A, Ints T, Ints G and Ints C representing the signal intensity values of bases A, T, G and C, respectively. After correction, in general, Ints A, Ints T, Ints G and Ints C have the same baseline, and the maximum value (max) in the array may be compared to a first preset value. If the maximum value is greater than or equal to the first preset value, it can be determined that the base type corresponding to the position on the image is the base corresponding to the maximum value, and namely the base at a corresponding position on the corresponding nucleic acid molecule is called to be the base corresponding to the maximum value; if the maximum value (max) in the array is less than the first preset value, it can be determined that the base type corresponding to the position on the image cannot be accurately called, and the base at the position of the corresponding nucleic acid molecule can be marked as N or that position can be left vacant, N being any one of A, T, G and C; in some examples, the reads containing N or vacant positions after basecalling may be further processed (for example, the base type represented by the N or vacant positions in the reads can be further inferred based on information of other reads, e.g., adjacent reads, or the reads are partially filtered) to improve utilization or quality of the resulting data.

In some examples, each value in {Ints A, Ints T, Ints G, Ints C} is a processed, e.g., normalized, value.

In one example, the quality score (QScore for short) of the four-dimensional data is calculated, and the QScore is prior probability in nature and can be calculated using known methods, such as referring to Ewing et al., Base-calling of automated sequencer traces using phred. I. Accuracy assessment., Genome Res. 1998 March, 8(3):175-85. Here, the inventors calculate QScore using a ratio of the maximum value to the total value in the corrected 4-dimensional data, and the obtained QScore is in the range of [0,40]. Specifically, QScore=(1.0×maxInts/sumInts−0.25)/0.75×40, where maxInts is the maximum value among Ints A, Ints T, Ints G and Ints C, and sumInts is the sum of Ints A, Ints T, Ints G and Ints C; accordingly, the first preset value is set to be 0.1, and if the QScore is greater than 0.1, the base type at the position is determined to be the base corresponding to maxInts. In this way, basecalling can be efficiently performed.

Above logic and/or steps shown in the flowcharts or described herein in other manners may be considered as a program list of executable instructions that are used to implement logical functions, and may be specifically implemented on any computer-readable storage medium, for use by an instruction execution system, device, or apparatus (for example, a computer-based system, a system comprising a processor, or another system that can fetch instructions from the instruction execution system, device, or apparatus and execute the instructions), or for use in combination with the instruction execution system, device or apparatus. For example, in one embodiment of the present application, provided is a computer-readable storage medium configured for storing a program executed by a computer, and executing the program comprises implementing the method according to any of the aforementioned embodiments. The computer-readable storage medium may be any device that may include, store, communicate, propagate, or transmit a program for use by an instruction execution system, device, or apparatus, or for use in combination with the instruction execution system, device or apparatus, including but no limited to read-only memories, magnetic disks, optical disks, or the like. More specifically, the computer-readable storage medium include the following (this list is not exhaustive): an electrical connection (an electrical device) with one or more buses, a portable computer cartridge (an magnetic device), a random-access memory (RAM), a read-only memory (ROM), an erasable programmable read-only memory (EPROM or flash memory), an optical fiber device, and a portable compact disc read-only memory (CDROM). In addition, the computer-readable storage medium may even be a piece of paper on which the programs can be printed or any other appropriate media; for example, the piece of paper or the other media may be optically scanned, and the program may be electrically acquired by processing such as edition, decoding, or any other appropriate means when necessary and then stored in a computer storage. The above description of the technical features and advantages of the method for basecalling according to any of the embodiments is also applicable to the computer-readable storage medium, and will not be repeated herein.

Further, in one embodiment of the present application, provided is a computer product comprising the computer-readable storage medium according to any of the aforementioned embodiments.

For example, in one embodiment of the present application, provided is system comprising the computer product according to any of the aforementioned embodiments and at least one processor configured for executing a program stored in the computer-readable storage medium.

For example, in one embodiment of the present application, provided is a computer program product comprising an instruction for calling one or more bases in a nucleic acid, and the instruction causes a computer to execute the method for calling one or more bases in a nucleic acid according to any of the aforementioned embodiments when the program is executed by the computer.

In one embodiment of the present application, provided is a system configured for performing the method for calling one or more bases in a nucleic acid according to any of the aforementioned embodiments.

Figure 21:
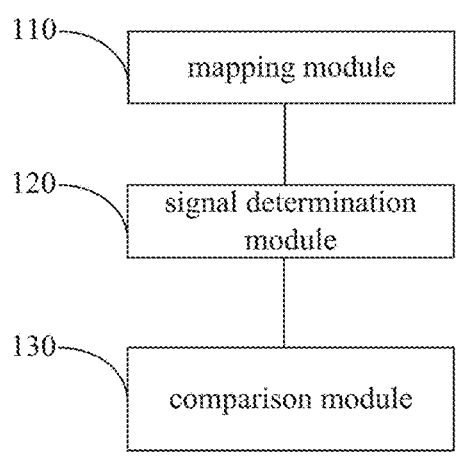
FIG. 21 shows a schematic diagram of a system 100 according to an embodiment of the present application.

Referring to FIG. 21, in one embodiment of the present application, provided is a system 100 comprising a plurality of modules, and the system is configured for performing the steps of the method for calling one or more bases in a nucleic acid according to any of the aforementioned embodiments. The system 100 comprises a mapping module 110, a signal determination module 120 and a comparison module 130. The mapping module 110 is configured for aligning coordinates of each spot in a spot set corresponding to a template to an image to be detected to determine a position of corresponding coordinates on the image to be detected. The spot set corresponding to the template is constructed based on a set of images, and each image in the set of images comprises a plurality of spots; the set of images and the image to be detected are all from sequencing and correspond to a same field of view; the sequencing comprises adding nucleotides for multiple cycles of sequencing, the set of images are from at least one cycle of sequencing, and at least a part of the signals are shown as at least a part of the spots on the set of images.

The signal determination module 120 is configured for determining intensity of a signal of the position of the corresponding coordinates on the image to be detected from the mapping module 110, the intensity being corrected intensity. The comparison module 130 is configured for comparing the intensity of the signal of the position of the corresponding coordinates on the image to be detected from the signal determination module 120 with a first preset value, and determining a base type corresponding to the position based on a comparison result to realize the basecalling.

It will be understood by those skilled in the art know that, in addition to implementing the controller or processor in a form of computer-readable program code, same functions can be implemented in a form of a logic gate, a switch, an application-specific integrated circuit, an editable logic controller, an embedded microcontroller, and the like by logically programming the steps. Therefore, the controller or processor may be regarded as a hardware component, and a device included in the controller or processor for implementing various functions may also be regarded as a structure in the hardware component. Alternatively, a device for implementing various functions may be regarded as both a software module for implementing the method and a structure in the hardware component.

The description of the technical features and advantages of the method for calling one or more bases in a nucleic acid in the aforementioned embodiments is also applicable to this system and will not be repeated here. It can be understood that additional technical features of the method for calling one or more bases in a nucleic acid in any of the aforementioned embodiments, including sub-steps, additional steps, and optional, alternative or preferred settings or processing can be implemented by allowing the system or modules of the system to further comprise units or modules or sub-units or sub-modules.

In some examples, the system 100 further comprises a spot set construction module configured for constructing the spot set corresponding to the template and connected to the mapping module 110.

In some other examples, the mapping module 110 comprises a spot set construction sub-module configured for constructing the spot set corresponding to the template and comprising: an image acquisition unit configured for sequentially or simultaneously adding four types of nucleotides into a reaction system for one cycle of sequencing to obtain a set of images, where the four types of nucleotides carry different labels that are excited to emit signals with different colors, the set of images comprise a first image, a second image, a third image and a fourth image, the first image, the second image, the third image and the fourth image are acquired from reaction signals of the four types of nucleotides in a same field of view, respectively, and the reaction system comprises the template and polymerase; a spot detection unit configured for detecting spots for the first image, the second image, the third image and the fourth image from the image acquisition unit separately to determine the spots of the images; an alignment unit configured for aligning the set of images; a merging unit configured for merging the spots on the aligned set of images from the alignment unit to obtain a primary spot set; and a spot set establishment unit configured for establishing spot sets corresponding to the four types of nucleotides, respectively, based on the primary spot set from the merging unit.

In some examples, when the four types of nucleotides are added to the reaction system simultaneously, the image acquisition unit acquires the signals by an imaging system to obtain the set of images and/or the image to be detected, and the imaging system comprises a first laser, a second laser, a first camera, and a second camera.

In some examples, the four types of nucleotides added by the image acquisition unit carry a first label, a second label, a third label and a fourth label, respectively; in the one cycle of sequencing: the first laser is started to excite the nucleotides, two of the four nucleotides emit a first signal and a second signal, respectively, and the first camera and the second camera synchronously operate and acquire the first signal and the second signal, respectively, to obtain the first image and the second image; and, the second laser is started to excite the nucleotides, the other two nucleotides of the four nucleotides emit a third signal and a fourth signal, respectively, and the first camera and the second camera synchronously operate and acquire the third signal and the fourth signal, respectively, to obtain the third image and the fourth image.

In some examples, the spot detection unit detects each image of the set of images using a k1×k2 matrix, which comprises: determining that a matrix with a relation midS between central intensity and edge intensity meeting a first preset condition corresponds to a spot; the central intensity reflects intensity of a central area of the matrix, the edge intensity reflects intensity of an edge area of the matrix, the central area and the edge area form the matrix, k1 and k2 are both natural numbers greater than 1, and the k1×k2 matrix comprises k1×k2 pixels.

In some examples, when the spot detection unit detects each image of the set of images using the k1×k2 matrix, k1 is equal to k2.

In some examples, when the spot detection unit detects each image of the set of images using the k1×k2 matrix, k1 and k2 are both odd numbers greater than 1.

When the spot detection unit detects each image of the set of images using the k1×k2 matrix, k1 and k2 are both odd numbers greater than 3, and the central area is a 3×3 area centered on a central pixel of the matrix.

In some examples, when the spot detection unit detects each image of the set of images using the k1×k2 matrix, the first preset condition is that midS≥S1, midS=midInt−sumInts(1: n)/n. midInt represents the central intensity, sumInts(1: n)/n represents the edge intensity, sumInts(1: n) represents the sum of pixel values of the $1^{st}$ to $N^{th}$ pixels of the edge area, n is a natural number not less than 4, and S1 is any value of [2, 4].

In some examples, the spot detection unit is configured for: convolving each image of the set of images to obtain convolved images; searching for all pixels containing peak values in a k3×k4 area in the convolved images, k3 and k4 being both natural numbers greater than 1, and the k3×k4 area containing k3×k4 pixels of the convolved images; and determining that a k5×k6 area meeting a second preset condition and centering on a peak pixel corresponds to a spot, the second preset condition being that a pixel value of the peak pixel of the k5×k6 area is not less than S2, k5 and k6 being both natural numbers greater than 1, and S2 being capable of being determined based on pixels of the convolved image.

In some examples, k3 is equal to k4, and/or k5 is equal to k6.

In some examples, k3 and k4 are both odd numbers greater than 1, and/or k5 and k6 are both odd numbers greater than 1.

In some examples, k3 and k4 are both odd numbers greater than 3, and/or k5 and k6 are both odd numbers greater than 3.

In some examples, S2 is not less than a median of all pixels of the convolved images sorted in ascending order of pixel values and/or not greater than the $80^{th}$ quantile of all pixels of the convolved images sorted in ascending order of pixel values.

In some examples, the spot detection unit further comprises screening spots of an original image based on intensity of areas where the spots are located on the image.

In some examples, the spot detection unit detects each image of the set of images using a k7×k8 matrix, which comprises: determining that a k7×k8 matrix where a plurality of pixel values in designated directions show monotonic fluctuation corresponds to a candidate spot; and screening the candidate spot using pixels of at least a part of the area in a corresponding k7×k8 matrix to determine the spot, k7 and k8 being both natural numbers greater than 1, and the k7×k8 matrix comprising k7×k8 pixels.

In some examples, k7 is equal to k8, and/or k7 and k8 are both odd numbers greater than 1.

In some examples, the mapping module 110 further comprises a sub-pixel coordinate determination sub-module configured for determining sub-pixel coordinates of the spot using a centroid method.

In some examples, the alignment unit performs the aligning using images from cycle M of sequencing.

In some examples, aligning the set of images comprises performing the aligning using images from cycle M of sequencing. M is, for example, greater than 20, 30 or 50.

In some examples, when the alignment unit performs the aligning using images from cycle M of sequencing, the images from the cycle M of sequencing comprise a fifth image, a sixth image, a seventh image and an eighth image. The fifth image, the sixth image, the seventh image and the eighth image correspond to the same type of nucleotide as the first image, the second image, the third image and the fourth image, respectively. Coordinate systems of the sixth image, the seventh image and the eighth image are converted by taking a coordinate system of the fifth image as a baseline, which comprises: dividing the fifth image and the sixth image separately into a group of blocks with the size of k9×k10 in the same way, k9 and k10 being both natural numbers greater than 30, and k9×k10 comprising k9×k10 pixels; determining an offset of each block of the sixth image relative to a corresponding block of the fifth image; and aligning the second image and the first image based on the offset.

In some examples, merging the spots on the aligned set of images performed by the merging unit comprises merging a plurality of spots within a preset range k11×k12 into one spot, k11 and k12 being both natural numbers greater than 1, and k11×k12 comprising k11×k12 pixels.

In some examples, the signal determination module 120 is configured for determining intensity of a signal of the position of the corresponding coordinates on the image to be detected. The intensity is corrected intensity, and the intensity correction comprises crosstalk correction and/or phase correction.

In some examples, the mapping module 110 aligns the image to be detected to the spot set corresponding to the template before the signal determination module 120 corrects the intensity.

In some examples, the intensity correction by the signal determination module 120 comprises crosstalk correction, the crosstalk correction being performed based on at least one of images from the same cycle of sequencing and corresponding to different types of nucleotides or bases.

In some examples, the crosstalk correction used by the signal determination module 120 in intensity correction comprises:
fitting signals of positions of a plurality of corresponding coordinates in a specific area of the image to be detected to obtain a fitting result; and correcting the signals of the positions of the corresponding coordinates on the image to be detected based on the fitting result. An image Xi and the image to be detected are from the same cycle of sequencing, the image Xi and the image to be detected correspond to the same field of view, and the image to be detected contains signals from a nucleotide corresponding to the image Xi.

In some examples, the fitting is linear fitting.

In some examples, the intensity correction by the signal determination module 120 comprises phase correction, the phase correction being performed based on at least one of images from adjacent cycles of sequencing and corresponding to the same type of nucleotide or base.

In some examples, the phase correction used by the signal determination module 120 in intensity correction comprises: fitting signals of positions of a plurality of corresponding coordinates in a specific area of the image to be detected to obtain a fitting result; and correcting the signals of the positions of the corresponding coordinates on the image to be detected based on the fitting result. An image Yj and the image to be detected are from two adjacent cycles of sequencing, the image Yj and the image to be detected correspond to the same field of view, and the image Yj and the image to be detected correspond to the same type of nucleotide.

The method, product and/or system of any of the embodiments of the present application allows for rapid and accurate basecalling and enables the determination of the order of nucleotides or bases of at least a part of the sequence of the template.

In the description of this specification, the description of the terms "one embodiment", "some embodiments", "schematic embodiments", "examples", "specific examples", "some examples" or the like, means that the particular features, structures, materials or characteristics described in reference to the embodiment or example are included in at least one embodiment or example of the present application. In this specification, the schematic description of the aforementioned terms do not necessarily refer to the same embodiment or example.

Moreover, the particular features, structures, materials or characteristics described may be combined in any embodiment or example in any appropriate manner.

Although the embodiments of the present application have been shown and described above, it is to be understood that the aforementioned embodiments are exemplary and are not to be construed as limiting the present application, and that those of ordinary skill in the art may make changes, modifications, replacements and variations to such embodiments, without departing from the scope of the present application.

What is claimed is:

1. A method for calling one or more bases in a nucleic acid by detecting an image obtained from sequencing, comprising:
aligning coordinates of each spot in a spot set corresponding to a template to a target image, to determine a position of corresponding coordinates on the target image;
determining intensity of a signal of the position of the corresponding coordinates on the target image, the intensity being corrected intensity; and
comparing the intensity of the signal of the position of the corresponding coordinates on the target image with a first preset value, and determining a base type corresponding to the position based on a comparison result to realize basecalling; wherein
the spot set corresponding to the template is constructed based on a set of images, and each image in the set of images comprises a plurality of spots;
the set of images and the target image are all from sequencing and correspond to a same field of view, and the sequencing comprises adding nucleotides;
the sequencing comprises multiple cycles of sequencing, the set of images are from at least one cycle of sequencing, and at least a part of signals are shown as at least a part of spots on the set of images.

2. The method according to claim 1, wherein when the sequencing is performed, four types of nucleotides carrying different labels are added, the different labels being excited to emit signals with different colors, and the spot set corresponding to the template is constructed by at least:
sequentially or simultaneously adding four types of nucleotides into a reaction system for one cycle of sequencing to obtain the set of images, wherein the set of images comprises a first image, a second image, a third image and a fourth image, the first image, the second image, the third image and the fourth image are acquired from reaction signals of the four types of nucleotides in a same field of view, respectively, and the reaction system comprises the template and polymerase;
performing spot detection for the first image, the second image, the third image and the fourth image separately to determine spots;
aligning the set of images;
merging the spots on the aligned set of images to obtain a primary spot set; and
establishing spot sets corresponding to the four types of nucleotides, respectively, based on the primary spot set.

3. The method according to claim 2, wherein the spot detection comprises detecting each image of the set of images using a k1×k2 matrix, by at least:
determining that a matrix with a relation midS between central intensity and edge intensity meeting a first preset condition corresponds to a spot, wherein the central intensity reflects intensity of a central area of the matrix, the edge intensity reflects intensity of an edge area of the matrix, the central area and the edge area form the matrix, k1 and k2 are both natural numbers greater than 1, and the k1×k2 matrix comprises k1×k2 pixels.

4. The method according to claim 2, wherein the spot detection comprises:
convolving each image of the set of images to obtain convolved images;
searching for all pixels containing peak values in a k3×k4 area in the convolved images, wherein k3 and k4 are both natural numbers greater than 1, and the k3×k4 area comprises k3×k4 pixels of the convolved images; and
determining that a k5×k6 area meeting a second preset condition and centering on a peak pixel corresponds to a spot, wherein the second preset condition is that a pixel value of the peak pixel of the k5×k6 area is not less than S2, wherein k5 and k6 are both natural numbers greater than 1, and S2 can be determined based on pixels of the convolved images.

5. The method according to claim 2, wherein the spot detection comprises detecting each image of the set of images using a k7×k8 matrix, by at least:
   determining that a k7×k8 matrix where a plurality of pixel values in designated directions show monotonic fluctuation corresponds to a candidate spot, and
   screening the candidate spot using pixels of at least a part of the area in a corresponding k7×k8 matrix to determine the spot, wherein k7 and k8 are both natural numbers greater than 1, and the k7×k8 matrix comprises k7×k8 pixels.

6. The method according to claim 2, wherein aligning the set of images comprises performing the aligning using images from cycle M of sequencing.

7. The method according to claim 6, wherein the images from the cycle M of sequencing comprise a fifth image, a sixth image, a seventh image and an eighth image, wherein the fifth image, the sixth image, the seventh image and the eighth image correspond to reaction signals of the same type of nucleotide as the first image, the second image, the third image and the fourth image, respectively;
   and wherein coordinate systems of the sixth image, the seventh image and the eighth image are converted by taking a coordinate system of the fifth image as a baseline, and by:
   dividing the fifth image and the sixth image separately into a group of blocks with a size of k9×k10 in a same way, k9 and k10 being both natural numbers greater than 30, and k9×k10 comprising k9×k10 pixels;
   determining an offset of each block of the sixth image relative to a corresponding block of the fifth image; and
   aligning the second image and the first image based on the offset.

8. The method according to claim 2, wherein the corrected intensity is determined based on at least one of crosstalk correction or phase correction.

9. The method according to claim 2, wherein the merging the spots on the aligned set of images comprises merging a plurality of spots within a preset range k11×k12 into one spot, k11 and k12 being both natural numbers greater than 1, and k11×k12 comprising k11×k12 pixels.

10. A computer program product, comprising instructions for calling one or more bases on a nucleic acid, wherein the instructions cause a computer to execute the method according to claim 1 when the program is executed by the computer.

11. A system, comprising:
   a mapping module configured for aligning coordinates of each spot in a spot set corresponding to a template to a target image, to determine a position of corresponding coordinates on the target image;
   a signal determination module configured for determining intensity of a signal of the position of the corresponding coordinates on the target image, the intensity being corrected intensity; and
   a comparison module configured for comparing the intensity of the signal of the position of the corresponding coordinates on the target image with a first preset value, and determining a base type corresponding to the position based on a comparison result to realize base-calling; wherein
   the spot set corresponding to the template is constructed based on a set of images, and each image in the set of images comprises a plurality of spots; the set of images and the target image are all from sequencing and correspond to a same field of view; the sequencing comprises adding nucleotides for multiple cycles of sequencing, the set of images are from at least one cycle of sequencing, and at least a part of signals are shown as at least a part of spots on the set of images.

12. The system according to claim 11, further comprising a spot set construction module configured for constructing the spot set corresponding to the template and connected to the mapping module.

13. The system according to claim 11, wherein the mapping module comprises a spot set construction sub-module configured for constructing the spot set corresponding to the template, and the spot set construction sub-module comprising:
   an image acquisition unit configured for sequentially or simultaneously adding four types of nucleotides into a reaction system for one cycle of sequencing to obtain a set of images, wherein the four types of nucleotides carry different labels that are excited to emit signals with different colors, the set of images comprises a first image, a second image, a third image and a fourth image, the first image, the second image, the third image and the fourth image are acquired from reaction signals of the four types of nucleotides in a same field of view, respectively, and the reaction system comprises the template and polymerase;
   a spot detection unit configured for detecting spots for the first image, the second image, the third image and the fourth image separately to determine spots;
   an alignment unit configured for aligning the set of images;
   a merging unit configured for merging the spots on the aligned set of images to obtain a primary spot set; and
   a spot set establishment unit configured for establishing spot sets corresponding to the four types of nucleotides, respectively, based on the primary spot set.

14. The system according to claim 13, wherein the spot detection unit is configured for:
   convolving each image of the set of images to obtain convolved images;
   searching for all pixels containing peak values in a k3×k4 area in the convolved images, wherein k3 and k4 are both natural numbers greater than 1, and the k3×k4 area comprises k3×k4 pixels of the convolved images; and
   determining that a k5×k6 area meeting a second preset condition and centering on a peak pixel corresponds to a spot, wherein the second preset condition is that a pixel value of the peak pixel of the k5×k6 area is not less than S2, wherein k5 and k6 are both natural numbers greater than 1, and S2 can be determined based on pixels of the convolved images.

15. The system according to claim 13, wherein the spot detection unit detects each image of the set of images using a k1×k2 matrix, by at least:
   determining that a matrix with a relation midS between central intensity and edge intensity meeting a first preset condition corresponds to a spot, wherein the central intensity reflects intensity of a central area of the matrix, the edge intensity reflects intensity of an edge area of the matrix, the central area and the edge area form the matrix, k1 and k2 are both natural numbers greater than 1, and the k1×k2 matrix comprises k1×k2 pixels.

16. The system according to claim 13, wherein the spot detection comprises detecting each image of the set of images using a k7×k8 matrix, by at least:
   determining that a k7×k8 matrix where a plurality of pixel values in designated directions show monotonic fluctuation corresponds to a candidate spot, and
   screening the candidate spot using pixels of at least a part of the area in a corresponding k7×k8 matrix to determine the spot, wherein k7 and k8 are both natural numbers greater than 1, and the k7×k8 matrix comprises k7×k8 pixels.

17. The system according to claim 13, wherein the alignment unit performs the aligning using images from cycle M of sequencing.

18. The system according to claim 17, wherein the images from the cycle M of sequencing comprise a fifth image, a sixth image, a seventh image and an eighth image, wherein the fifth image, the sixth image, the seventh image and the eighth image correspond to reaction signals of the same type of nucleotide as the first image, the second image, the third image and the fourth image, respectively;
   and wherein coordinate systems of the sixth image, the seventh image and the eighth image are converted by taking a coordinate system of the fifth image as a baseline, and by:
   dividing the fifth image and the sixth image separately into a group of blocks with a size of k9×k10 in a same way, k9 and k10 being both natural numbers greater than 30, and k9×k10 comprising k9×k10 pixels;
   determining an offset of each block of the sixth image relative to a corresponding block of the fifth image; and
   aligning the second image and the first image based on the offset.

19. The system according to claim 13, wherein merging the spots on the aligned set of images performed by the merging unit comprises merging a plurality of spots within a preset range k11×k12 into one spot, k11 and k12 being both natural numbers greater than 1, and k11×k12 comprising k11×k12 pixels.

20. The system according to claim 13, wherein the corrected intensity is determined based on at least one of crosstalk correction or phase correction.

* * * * *